United States Patent
Song et al.

(10) Patent No.: US 11,887,697 B2
(45) Date of Patent: Jan. 30, 2024

(54) GRAPHICAL USER INTERFACE DISPLAYING RELATEDNESS BASED ON SHARED DNA

(71) Applicant: Ancestry.com DNA, LLC, Lehi, UT (US)

(72) Inventors: Shiya Song, San Mateo, CA (US); Neal Craig Varner, Highland, UT (US); Ross E. Curtis, Cedar Hills, UT (US); Brian Jerel Kerr, Pleasant Grove, UT (US); Kelly McCloy Becker, Salt Lake City, UT (US); Brett Frederick Jorgensen, Draper, UT (US); Bryce Damon Ririe, Highland, UT (US); Michael Joseph Mulligan, Dublin (IE); Justin Matthew Robert Van Dyke, Dublin (IE); Michaela Black Bonkemeyer, Burlington, CT (US)

(73) Assignee: Ancestry.com DNA, LLC, Lehi, UT (US)

( * ) Notice: Subject to any disclaimer, the term of this patent is extended or adjusted under 35 U.S.C. 154(b) by 0 days.

(21) Appl. No.: 18/045,138

(22) Filed: Oct. 7, 2022

(65) Prior Publication Data
US 2023/0116793 A1    Apr. 13, 2023

Related U.S. Application Data

(63) Continuation of application No. 16/803,219, filed on Feb. 27, 2020, now Pat. No. 11,482,306.
(Continued)

(51) Int. Cl.
*G16B 45/00* (2019.01)
*G16B 40/30* (2019.01)
*G16B 40/20* (2019.01)

(52) U.S. Cl.
CPC ............. *G16B 45/00* (2019.02); *G16B 40/20* (2019.02); *G16B 40/30* (2019.02)

(58) Field of Classification Search
None
See application file for complete search history.

(56) References Cited

U.S. PATENT DOCUMENTS

| | | | |
|---|---|---|---|
| 718,127 | A | 1/1903 | Holmgren |
| D169,994 | S | 7/1953 | Soffer et al. |

(Continued)

FOREIGN PATENT DOCUMENTS

KR    10-2009-0022519 A    3/2009

OTHER PUBLICATIONS

Meulenbelt, I. et al. "High-Yield Noninvasive Human Genomic DNA Isolation Method for Genetic Studies in Geographically Dispersed Families and Populations," American Journal of Human Genetics, 1995, vol. 57, No. 1252-1254, 3 pages.
(Continued)

*Primary Examiner* — Kee M Tung
*Assistant Examiner* — Jed-Justin Imperial
(74) *Attorney, Agent, or Firm* — Fenwick & West LLP

(57) ABSTRACT

A user may select one or more potential common ancestors with a DNA match to view the target individual's relationship with them. The process may include identifying, from a first genealogical profile of the target individual. A first individual has a first linkage that connects the target individual towards the selected potential common ancestor. The process may also include identifying, from a second genealogical profile of the DNA match, a second individual who has a second linkage that connects the DNA match towards the selected potential common ancestor. The process may further include connecting the first linkage and the second linkage with the selected potential common ancestor by
(Continued)

adding one or more individuals whose profiles are retrieved from other searchable genealogical profiles stored in the online system. With the nodes and connections available, the process may generate a map of visual connections between the target individual and the DNA match.

20 Claims, 14 Drawing Sheets

Related U.S. Application Data

(60) Provisional application No. 62/882,438, filed on Aug. 2, 2019, provisional application No. 62/811,505, filed on Feb. 27, 2019.

(56) References Cited

U.S. PATENT DOCUMENTS

| | | |
|---|---|---|
| D175,257 S | 8/1955 | Hopkins |
| 2,793,776 A | 5/1957 | Lipari |
| D196,112 S | 8/1963 | Esser |
| 3,831,742 A | 8/1974 | Gardella et al. |
| 4,131,016 A | 12/1978 | Layton |
| 4,184,483 A | 1/1980 | Greenspan |
| 4,217,798 A | 8/1980 | McCarthy et al. |
| 4,301,812 A | 11/1981 | Layton et al. |
| 4,312,950 A | 1/1982 | Snyder et al. |
| D277,736 S | 2/1985 | Long |
| D286,546 S | 11/1986 | Funahashi |
| 4,935,342 A | 6/1990 | Seligson et al. |
| 4,982,553 A | 1/1991 | Itoh |
| D330,011 S | 10/1992 | Miller et al. |
| 5,283,038 A | 2/1994 | Seymour |
| 5,393,496 A | 2/1995 | Seymour |
| 5,396,986 A | 3/1995 | Fountain et al. |
| D362,623 S | 9/1995 | Ma |
| 5,714,341 A | 2/1998 | Thieme et al. |
| D392,187 S | 3/1998 | King |
| 5,736,322 A | 4/1998 | Goldstein |
| 5,736,355 A | 4/1998 | Dyke et al. |
| 5,830,154 A | 11/1998 | Goldstein et al. |
| 5,830,410 A | 11/1998 | Thieme et al. |
| D412,107 S | 7/1999 | Bosshardt |
| 5,927,549 A | 7/1999 | Wood |
| 5,933,498 A | 8/1999 | Schneck et al. |
| 6,003,728 A | 12/1999 | Elliott |
| 6,048,091 A | 4/2000 | McIntyre et al. |
| 6,152,296 A | 11/2000 | Shih |
| D437,786 S | 2/2001 | van Swieten et al. |
| 6,228,323 B1 | 5/2001 | Asgharian et al. |
| 6,362,473 B1 * | 3/2002 | Germanus ........... G06F 16/9027 250/282 |
| 6,428,962 B1 | 8/2002 | Naegele |
| 6,458,546 B1 | 10/2002 | Baker |
| D470,240 S | 2/2003 | Niedbala et al. |
| D471,234 S | 3/2003 | Okutani |
| 6,543,612 B2 | 4/2003 | Lee et al. |
| 6,548,256 B2 | 4/2003 | Lienau et al. |
| D474,280 S | 5/2003 | Niedbala et al. |
| 6,627,152 B1 | 9/2003 | Wong |
| 6,760,731 B2 | 7/2004 | Huff |
| 6,786,330 B2 | 9/2004 | Mollstam et al. |
| D507,351 S | 7/2005 | Birnboim |
| 6,939,672 B2 | 9/2005 | Lentrichia et al. |
| 6,992,182 B1 | 1/2006 | Müller et al. |
| D515,435 S | 2/2006 | Muehlhausen |
| 7,055,685 B1 | 6/2006 | Patterson et al. |
| D537,416 S | 2/2007 | Fortin et al. |
| 7,178,683 B2 | 2/2007 | Birkmayer et al. |
| 7,214,484 B2 | 5/2007 | Weber et al. |
| 7,297,485 B2 | 11/2007 | Bornarth et al. |
| 7,303,876 B2 | 12/2007 | Greenfield et al. |
| D573,465 S | 7/2008 | Kogure et al. |
| D574,507 S | 8/2008 | Muir et al. |
| D584,357 S | 1/2009 | Oka |
| 7,482,116 B2 | 1/2009 | Birnboim |
| D586,856 S | 2/2009 | Yagyu |
| 7,537,132 B2 | 5/2009 | Marple et al. |
| 7,544,468 B2 | 6/2009 | Goldstein et al. |
| 7,589,184 B2 | 9/2009 | Hogan et al. |
| 7,645,424 B2 | 1/2010 | O'Donovan |
| D612,730 S | 3/2010 | Rushe |
| 7,748,550 B2 | 7/2010 | Cho |
| 7,854,104 B2 | 12/2010 | Cronin et al. |
| 7,858,396 B2 | 12/2010 | Corstjens et al. |
| D631,350 S | 1/2011 | Beach et al. |
| D631,553 S | 1/2011 | Niedbala et al. |
| D640,794 S | 6/2011 | Sunstrum et al. |
| D640,795 S | 6/2011 | Jackson et al. |
| 7,998,757 B2 | 8/2011 | Darrigrand et al. |
| 8,038,668 B2 | 10/2011 | Scott et al. |
| 8,062,908 B2 | 11/2011 | Mink et al. |
| 8,158,357 B2 | 4/2012 | Birnboim et al. |
| 8,221,381 B2 | 7/2012 | Muir et al. |
| D673,265 S | 12/2012 | Nonnemacher et al. |
| 8,425,864 B2 | 4/2013 | Haywood et al. |
| 8,431,384 B2 | 4/2013 | Hogan et al. |
| 8,470,536 B2 | 6/2013 | Birnboim et al. |
| D693,682 S | 11/2013 | Bahri et al. |
| 8,673,239 B2 | 3/2014 | Niedbala et al. |
| 8,728,414 B2 | 5/2014 | Beach et al. |
| D718,127 S | 11/2014 | Moriyama et al. |
| 9,040,675 B2 | 5/2015 | Bales et al. |
| 9,072,499 B2 | 7/2015 | Birnboim et al. |
| 9,079,181 B2 | 7/2015 | Curry et al. |
| D743,044 S | 11/2015 | Jackson et al. |
| D743,571 S | 11/2015 | Jackson et al. |
| 9,207,164 B2 | 12/2015 | Muir et al. |
| D757,546 S | 5/2016 | Seifer |
| 9,410,147 B2 | 8/2016 | Gundling |
| 9,416,356 B2 | 8/2016 | Gundling |
| 9,523,115 B2 | 12/2016 | Birnboim |
| D775,953 S | 1/2017 | Ruthe-Steinsiek |
| D777,111 S | 1/2017 | Zantout et al. |
| 9,732,376 B2 | 8/2017 | Oyler et al. |
| 9,757,179 B2 | 9/2017 | Formica |
| D811,882 S | 3/2018 | Gundersen |
| 10,000,795 B2 | 6/2018 | Birnboim et al. |
| D843,834 S | 3/2019 | Gundersen |
| D850,647 S | 6/2019 | Jackson et al. |
| 10,435,735 B2 | 10/2019 | Birnboim et al. |
| 2001/0041327 A1 | 11/2001 | Gross |
| 2003/0089627 A1 | 5/2003 | Chelles et al. |
| 2004/0132091 A1 | 7/2004 | Ramsey et al. |
| 2006/0201948 A1 | 9/2006 | Ellson et al. |
| 2007/0170142 A1 | 7/2007 | Cho |
| 2007/0178500 A1 | 8/2007 | Martin et al. |
| 2007/0218429 A1 | 9/2007 | Kolo et al. |
| 2007/0239802 A1 | 10/2007 | Razdow et al. |
| 2008/0068401 A1 * | 3/2008 | Albrecht ............ G06F 16/9577 707/E17.121 |
| 2008/0108027 A1 | 5/2008 | Sallin |
| 2008/0270431 A1 | 10/2008 | Garbero |
| 2009/0024060 A1 | 1/2009 | Darrigrand et al. |
| 2009/0216213 A1 | 8/2009 | Muir et al. |
| 2010/0099149 A1 | 4/2010 | Birnboim et al. |
| 2010/0258457 A1 | 10/2010 | Seelhofer |
| 2011/0020195 A1 | 1/2011 | Luotola |
| 2011/0207621 A1 | 8/2011 | Montagu et al. |
| 2011/0212002 A1 | 9/2011 | Curry et al. |
| 2012/0024861 A1 | 2/2012 | Otsuka et al. |
| 2012/0024862 A1 | 2/2012 | Otsuka et al. |
| 2012/0046574 A1 | 2/2012 | Skakoon |
| 2012/0061392 A1 | 3/2012 | Beach et al. |
| 2013/0092690 A1 | 4/2013 | Skakoon |
| 2013/0149707 A1 | 6/2013 | Sorenson et al. |
| 2013/0164738 A1 | 6/2013 | Becker et al. |
| 2014/0278138 A1 * | 9/2014 | Barber ............ G06F 16/24575 702/19 |
| 2014/0316302 A1 | 10/2014 | Nonnemacher et al. |
| 2015/0056716 A1 | 2/2015 | Oyler et al. |
| 2016/0262679 A1 | 9/2016 | Ivosevic et al. |
| 2016/0350479 A1 | 12/2016 | Han et al. |

(56) References Cited

U.S. PATENT DOCUMENTS

| | | |
|---|---|---|
| 2017/0001191 A1 | 1/2017 | Biadillah et al. |
| 2017/0072393 A1 | 3/2017 | Jackson et al. |
| 2017/0130219 A1 | 5/2017 | Birnboim et al. |
| 2017/0166955 A1 | 6/2017 | Birnboim et al. |
| 2017/0213127 A1* | 7/2017 | Duncan ............... G16B 50/30 |
| 2017/0226469 A1 | 8/2017 | Birnboim et al. |
| 2017/0277827 A1 | 9/2017 | Granka et al. |
| 2019/0151842 A1 | 5/2019 | Williams et al. |
| 2019/0210778 A1 | 7/2019 | Muir et al. |
| 2019/0358628 A1 | 11/2019 | Curry et al. |
| 2020/0380015 A1* | 12/2020 | Gray .................... G16H 70/60 |

OTHER PUBLICATIONS

PCT International Search Report and Written Opinion, PCT Patent Application No. PCT/IB2020/051694, dated Jun. 12, 2020, 12 pages.

European Patent Office, Extended European Search Report, European Patent Application No. 20762645.8, dated Oct. 20, 2022, 10 pages.

* cited by examiner

*FIG. 4*

| Home Trees Search DNA Help Extras |

< DNA matches for Neal

Group: | All matches ∨ |

+ Create custom group
◇ Grandma Hunt
◈ Grandma Wilson
◉ Mom's Group
◍ Shared w/ Dawn

All matches
Close matches–4th cousins or closer
Distant matches
New matches
Starred matches
Hidden matches
Shared matches with mother

Filtered by: | Add a filter ∨ |

Parent/Child
Shared DNA: 3,461 cM across 67 segments

Parent/Child
Shared DNA: 3,460 cM across 56 segments

Sister
Shared DNA: 2,715 cM across 62 segments

Brother
Shared DNA: 2,672 cM across 61 segments

Sister
Shared DNA: 2,617 cM across 52 segments

Brother
Shared DNA: 2,607 cM across 60 segments

Close Family-1st Cousin
Shared DNA: 1,901 cM across 47 segments

April

Phil

Full Sibling

Jean 911, 912, 910

Neal's DNA Matches

DNA matches for Neal

Home Trees Search DNA Help Extras

🛒 CART ✕

930

| | | | 📍 Map | 🔍 Search |

Group: All matches ⌄  Filtered by: 🍃 Common ancestors ⌄

931

Full Sibling

👤 Rachel — Sister
Shared DNA: 2,715 cM across 62 segments ⓘ
🍃 61,671 people Common ancestor
Both Sides
⦿ ○ ○ Add/edit groups

Close Family

👤 Cory — Close Family-1st Cousin
Shared DNA: 1,803 cM across 74 segments ⓘ
🍃 123 People Common ancestor
Mother's Side
⦿ ○ ○ Add/edit groups 👤 Lori — Close Family-1st Cousin
Shared DNA: 1,737 cM across 58 segments ⓘ
🍃 16,322 People Common ancestor
Mother's Side
⦿ ○ ○ Add/edit groups 👤 Karen — Close Family-1st Cousin
Shared DNA: 1,624 cM across 56 segments ⓘ
🍃 163 People Common ancestor
Father's Side
⦿ ○ ○ Add/edit groups 👤 Gayle — Close Family-1st Cousin
Shared DNA: 1,327 cM across 55 segments ⓘ
🍃 7 People Common ancestor
Father's Side
⦿ ○ ○ Add/edit groups

1st Cousins

👤 Olivia — 1st-2nd Cousin
Shared DNA: 1,007 cM across 40 segments ⓘ
🍃 123 People Common ancestor
Mother's Side
⦿ ○ ○ Add/edit groups 👤 Samuel — 1st-2nd Cousin
Shared DNA: 921 cM across 39 segments ⓘ
🍃 103 People Common ancestor
Mother's Side
⦿ ○ ○ Add/edit groups

*FIG. 9C*

GRAPHICAL USER INTERFACE DISPLAYING RELATEDNESS BASED ON SHARED DNA

CROSS-REFERENCE TO RELATED APPLICATIONS

The present application is a continuation of Ser. No. 16/803,219, filed on Feb. 27, 2020, which claims the benefit of U.S. Provisional Patent Application No. 62/811,505, filed on Feb. 27, 2019 and U.S. Provisional Patent Application No. 62/882,438, filed on Aug. 2, 2019. All of the foregoing are hereby incorporated by reference in their entirety.

FIELD

The disclosed embodiments relate to computer software for identification of family relationships based on genetical and genealogical records.

BACKGROUND

Human beings are similar and unique at the same time. Genetically, human beings are almost entirely identical with each other. However, even small differences in human DNA may be responsible for observed variations between individuals, which makes each person a unique individual. Therefore, individuals might be interested in finding what is unique about themselves. Individuals who are interested in learning more about their family history may conduct genealogical research.

Generally, researchers build family trees by collecting information about known ancestors, including but not limited to, birth and death dates, locations, spouses, offspring and the like. The primary source of the information is usually passed down by individuals within families. Individuals may have limited knowledge about families who are related with them but with whom they have lost connections. Therefore, it is sometimes challenging for individuals to gain comprehensive knowledge about their family histories outside their own families through search genealogical records.

SUMMARY

In one embodiment, a computer-implemented process for identifying potential common ancestors and potential DNA matches is described. In one embodiment, one or more potential common ancestors between a DNA match and a target individual are transmitted for display at an electronic device. A user may select one or more of the potential common ancestors to view the target individual's relationship with the selected potential common ancestors. The process may include identifying, from a first genealogical profile of the target individual stored at an online system, a first individual who has a first linkage that connects the target individual towards the selected potential common ancestor. The process may also include identifying, from a second genealogical profile of the DNA match stored at the online system, a second individual who has a second linkage that connects the DNA match towards the selected potential common ancestor. The process may further include connecting the first linkage and the second linkage with the selected potential common ancestor by adding one or more individuals whose profiles are retrieved from other searchable genealogical profiles stored in the online system. With the nodes and connections available, the process may include generating a map of visual connections between the target individual and the DNA match through the selected potential common ancestor. The map may include the first linkage, the second linkage, and the added one or more individuals.

In one embodiment, a computer implemented process for determining a confidence level of relatedness between a focal individual and a target potential relative is also described. The process may include retrieving one or more pedigrees that include the target potential relative. The process may also include identifying, from the one or more pedigrees, descendants of the target potential relative who has genetic datasets available, each descendant indicated by at least one of the pedigrees as a descendant of the target potential relative, the descendants including the focal individual. The process may further include identifying one or more branches from the one or more pedigrees, each of the identified branches being a branch of descendants of the target potential relative and including one or more descendants who have the genetic datasets available. The process may further include identifying, for each branch, one or more pairwise genetic relationships related to the branch, wherein a pairwise genetic relationship is between two descendants of the target potential relative. A pairwise genetic relationship related to the branch may be either (i) between one of the descendants in the branch and the focal individual or (ii) between one of the descendants in the cousin branch and a surrogate of the focal individual selected from one or more potential surrogates. The process may further include determining, for each branch and each of the pairwise genetic relationships related to the branch, a relationship score of the pairwise genetic relationship based on total length of shared identity-by-descent (IBD) segments between the pair of descendants in the pairwise genetic relationship, the total length of shared IBD segments determined from the genetic datasets of the pair. The process may further include combining, for each branch, one or more relationship scores to generate a combined relationship score representing relatedness of the focal individual with the branch. The process may further include providing a result of the confidence level of relatedness between the focal individual and the target potential relative based on one or more of the combined relationship scores that represent relatedness of the focal individual with the one or more branches of descendants of the target potential relative.

In yet another embodiment, a non-transitory computer readable medium that is configured to store instructions is described. The instructions, when executed by one or more processors, cause the one or more processors to perform a process that includes steps described in the above computer-implemented methods or described in any embodiments of this disclosure. In yet another embodiment, a system may include one or more processors and a storage medium that is configured to store instructions. The instructions, when executed by one or more processors, cause the one or more processors to perform a process that includes steps described in the above computer-implemented methods or described in any embodiments of this disclosure.

BRIEF DESCRIPTION OF THE DRAWINGS

FIG. 4 is an example graphical user interface that displays one or more common ancestors, in accordance with an embodiment.

FIGS. 9A-C are example graphical user interface interfaces where a user can view a subgroup of DNA matches by enforcing various type of criteria, in accordance with an embodiment.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

The figures (FIGS.) and the following description relate to preferred embodiments by way of illustration only. One of skill in the art may recognize alternative embodiments of the structures and methods disclosed herein as viable alternatives that may be employed without departing from the principles of what is disclosed.

Reference will now be made in detail to several embodiments, examples of which are illustrated in the accompanying figures. It is noted that wherever practicable similar or like reference numbers may be used in the figures and may indicate similarity or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Configuration Overview

Example System Environment

Figure 1:
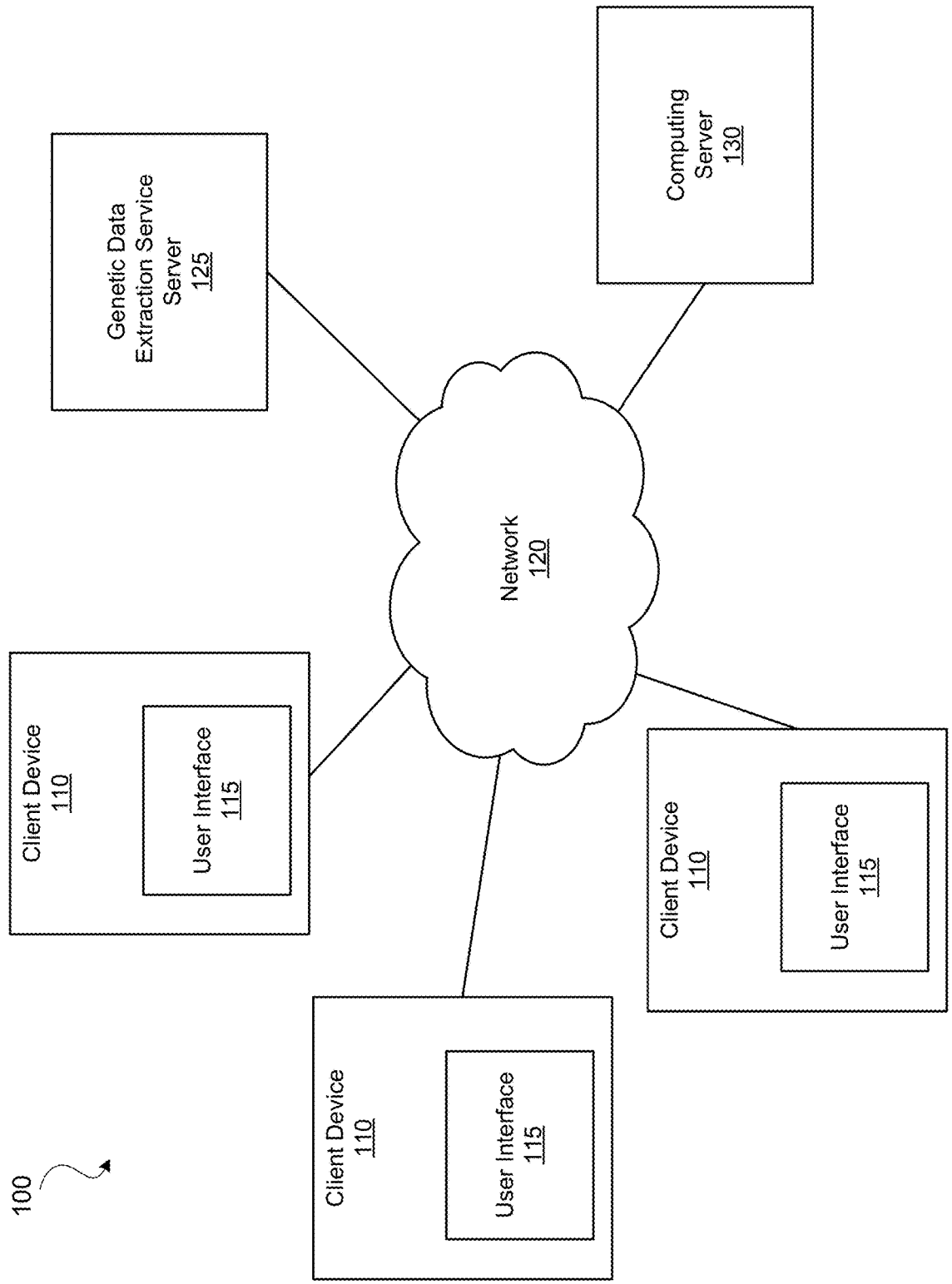
FIG. 1 illustrates a diagram of a system environment of an example computing system, in accordance with an embodiment.

FIG. 1 illustrates a diagram of a system environment 100 of an example computing server 130, in accordance with an embodiment. The system environment 100 shown in FIG. 1 includes one or more client devices 110, a network 120, a genetic data extraction service server 125, and a computing server 130. In various embodiments, the system environment 100 may include fewer or additional components. The system environment 100 may also include different components.

The client devices 110 are one or more electronic devices capable of receiving user input as well as transmitting and/or receiving data via a network 120. Example electronic devices include desktop computers, laptop computers, personal digital assistants (PDAs), smartphones, tablets, wearable electronic devices (e.g., smartwatches), smart household appliance (e.g., smart televisions, smart speakers, smart home hubs), Internet of Things (IoT) devices or other suitable electronic devices. A client device 110 communicates to other components via the network 120. Users may be customers of the computing server 130 or any individuals who access the system of the computing server 130, such as an online website or a mobile application. A first user may grant a second user full access to the first user's account and the second user will have access to the first user's information. In one embodiment, a client device 110 executes an application that launches a graphical user interface (GUI) for a user of the client device 110 to interact with the computing server 130. The GUI may be an example of a user interface 115. A client device 110 may also execute a web browser application to enable interactions between the client device 110 and the computing server 130 via the network 120. In another embodiment, the user interface 115 may take the form of a software application published by the computing server 130 and installed on the user device 110. In yet another embodiment, a client device 110 interacts with the computing server 130 through an application programming interface (API) running on a native operating system of the client device 110, such as IOS or ANDROID.

The network 120 provides connections to the components of the system environment 100 through one or more sub-networks, which may include any combination of local area and/or wide area networks, using both wired and/or wireless communication systems. In one embodiment, a network 120 uses standard communications technologies and/or protocols. For example, a network 120 may include communication links using technologies such as Ethernet, 802.11, worldwide interoperability for microwave access (WiMAX), 3G, 4G, Long Term Evolution (LTE), 5G, code division multiple access (CDMA), digital subscriber line (DSL), etc. Examples of network protocols used for communicating via the network 120 include multiprotocol label switching (MPLS), transmission control protocol/Internet protocol (TCP/IP), hypertext transport protocol (HTTP), simple mail transfer protocol (SMTP), and file transfer protocol (FTP). Data exchanged over a network 120 may be represented using any suitable format, such as hypertext markup language (HTML) or extensible markup language (XML). In some embodiments, all or some of the communication links of a network 120 may be encrypted using any suitable technique or techniques such as secure sockets layer (SSL), transport layer security (TLS), virtual private networks (VPNs), Internet Protocol security (IPsec), etc. The network 120 also includes links and packet switching networks such as the Internet.

Individuals, who may be customers of a company operating the computing server 130, provide biological samples for analysis of their genetic data. Individuals may also be referred to as users. A target individual may be an individual who is the target of the study of family history. In one embodiment, an individual uses a sample collection kit to provide a biological sample (e.g., saliva, blood, hair, tissue) from which genetic data is extracted and determined according to nucleotide processing techniques such as amplification and sequencing. Amplification may include using polymerase chain reaction (PCR) to amplify segments of nucleotide samples. Sequencing may include sequencing of deoxyribonucleic acid (DNA) sequencing, ribonucleic acid (RNA) sequencing, etc. Suitable sequencing techniques may include Sanger sequencing and massively parallel sequencing such as various next-generation sequencing (NGS) techniques including whole genome sequencing, pyrosequencing, sequencing by synthesis, sequencing by ligation, and ion semiconductor sequencing. In one embodiment, a set of SNPs (e.g., 300,000) that are shared between different array platforms (e.g., Illumina OmniExpress Platform and Illumina HumanHap 650Y Platform) may be obtained as the genetic data. Genetic data extraction service server 125 receives biological samples from users of the computing server 130. The genetic data extraction service server 125 performs sequencing of the biological samples and determines the base pair sequences of the individuals. The genetic data extraction service server 125 generates the genetic data of the individuals based on the sequencing results. The genetic data may include data sequenced from DNA or RNA and may include base pairs from coding and/or noncoding regions of DNA.

The genetic data may take different forms. For example, in one embodiment, the genetic data may be the base pair sequence of an individual. The base pair sequence may include the whole genome or a part of the genome such as certain genetic loci of interest. In another embodiment, the genetic data extraction service server 125 may determine genotypes from sequencing results, for example by identifying genotype values of single nucleotide polymorphisms (SNPs) present within the DNA. The results in this example may include a sequence of genotypes corresponding to various SNP sites. A SNP site may also be referred to as a SNP loci. A genetic locus is a segment of a genetic sequence. A locus can be a single site or a longer stretch. The segment can be a single base long or multiple bases long. In one embodiment, the genetic data extraction service server 125 may perform data pre-processing of the genetic data to convert raw sequences of base pairs to sequences of genotypes at target SNP sites. Since a typical human genome may differ from a reference human genome at only several million SNP sites (as opposed to billions of base pairs in the whole genome), the genetic data extraction service server 125 may extract only the genotypes at a set of target SNP sites and transmit the extracted data to the computing server 130 as the genetic dataset of an individual.

The computing server 130 performs various analyses of the genetic data, genealogical data, and users' survey responses to generate results regarding the phenotypes and genealogy of users of computing server 130. Depending on the embodiments, the computing server 130 may also be referring to as an online server, a personal genetic service server, a genealogy server, a family tree building server, and/or a social networking system. The computing server 130 receives genetic data from the genetic data extraction service server 125 and stores the genetic data in the data store of the computing server 130. The computing server 130 may analyze the data to generate results regarding the genetics or genealogy of users. The results regarding the genetics or genealogy of users may include the ethnicity compositions of users, paternal and maternal genetic analysis, identification or suggestion of potential family relatives, ancestor information, analyses of DNA data, potential or identified traits such as phenotypes of users (e.g., diseases, appearance traits, other genetic characteristics, and other non-genetic characteristics including social characteristics), etc. The computing server 130 may present or cause the user interface 115 to present the results to the users through a GUI displayed at the client device 110. The results may include graphical elements, textual information, data, charts, and other elements such as family trees.

In one embodiment, the computing server 130 also allows various users to create one or more genealogical profiles of the user. The genealogical profile may include a list of individuals (e.g., ancestors, relatives, friends, and other people of interest) who are added or selected by the user or suggested by the computing server 130 based on the genealogical records and/or genetic records. The user interface 115 controlled by or in communication with the computing server 130 may display the individuals in a list or as a family tree such as in the form of a pedigree chart. In one embodiment, subject to user's privacy setting and authorization, the computing server 130 may allow information generated from the user's genetic dataset to be linked to the user profile and to one or more of the family trees. The users may also authorize the computing server 130 to analyze their genetic dataset and allow their profiles to be discovered by other users.

Example Computing Server Architecture

Figure 2:
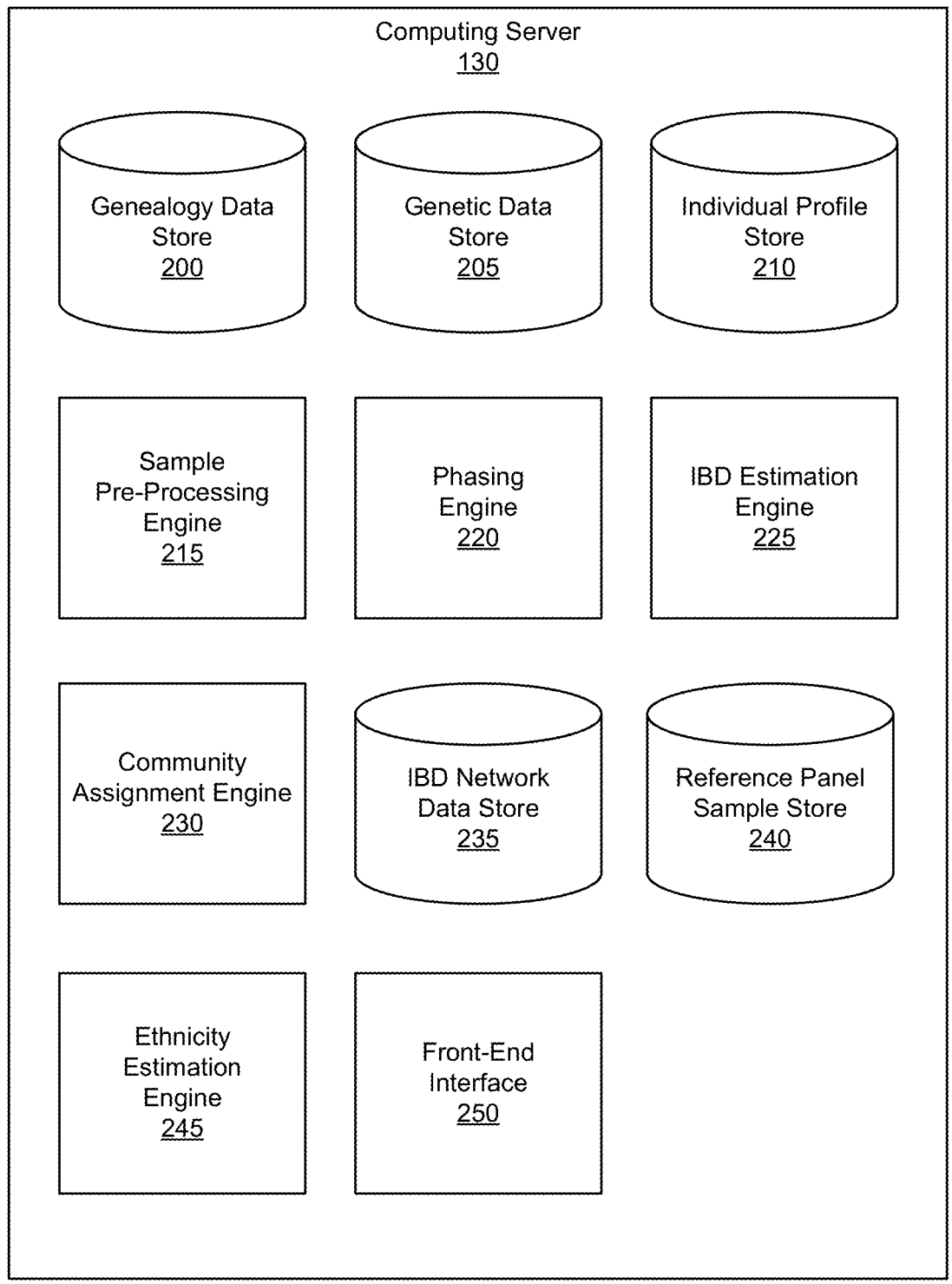
FIG. 2 is a block diagram of an architecture of an example computing system, in accordance with an embodiment.

FIG. 2 is a block diagram of an architecture of an example computing server 130, in accordance with an embodiment. In the embodiment shown in FIG. 2, the computing server 130 includes a genealogy data store 200, a genetic data store 205, an individual profile store 210, a sample pre-processing engine 215, a phasing engine 220, an identity by descent (IBD) estimation engine 225, a community assignment engine 230, an IBD network data store 235, a reference panel sample store 240, an ethnicity estimation engine 245, and a front-end interface 250. The functions of the computing server 130 may be distributed among the elements in a different manner than described. In various embodiments, the computing server 130 may include different components and fewer or additional components. Each of the various data stores may be a single storage device, a server controlling multiple storage devices, or a distributed network that is accessible through multiple nodes (e.g., a cloud storage system).

The computing server 130 stores various data of different individuals, including genetic data, genealogical data, and survey response data. The computing server 130 processes the genetic data of users to identify shared identity-by-descent (IBD) segments between individuals. The genealogical data and survey response data may be part of user profile data. The amount and type of user profile data stored for each user may vary based on the information of a user, which is provided by the user as she creates an account and profile at a system operated by the computing server 130 and continues to build her profile, family tree, and social network at the system and to link her profile with her genetic data. Users may provide data via the user interface 115 of a client device 110. Initially and as a user continues to build her genealogical profile, the user may be prompted to answer questions related to basic information of the user (e.g., name, date of birth, birthplace, etc.) and later more advanced questions that may be useful for obtaining additional genealogical data. The computing server 130 may also include survey questions regarding various traits of the users such as the users' phenotypes, characteristics, preferences, habits, lifestyle, environment, etc.

Genealogical data may be stored in the genealogical data store 200 and may include various types of data that are related to tracing family relatives of users. Examples of genealogical data include names (first, last, middle, suffixes), gender, birth locations, date of birth, date of death, marriage information, spouse's information kinships, family history, dates and places for life events (e.g., birth and death), other vital data, and the like. In some instances, family history can take the form of a pedigree of an individual (e.g., the recorded relationships in the family). The family tree information associated with an individual may include one or more specified nodes. Each node in the family tree represents the individual, an ancestor of the individual who might have passed down genetic material to the individual, and the individual's other relatives including siblings, cousins, offspring in some cases. Genealogical data may also include connections and relationships among users of the computing server 130. The information related to the connections among a user and her relatives that may be associated with a family tree may also be referred to as pedigree data or family tree data.

In addition to user-input data, genealogical data may also take other forms that are obtained from various sources such as public records and third-party data collectors. For example, genealogical records from public sources include birth records, marriage records, death records, census records, court records, probate records, adoption records, obituary records, etc. Likewise, genealogical data may include data from one or more of a pedigree of an individual, the Ancestry World Tree system, a Social Security Death Index database, the World Family Tree system, a birth certificate database, a death certificate database, a marriage certificate database, an adoption database, a draft registration database, a veterans database, a military database, a property records database, a census database, a voter registration database, a phone database, an address database, a newspaper database, an immigration database, a family history records database, a local history records database, a business registration database, a motor vehicle database, and the like.

Furthermore, the genealogical data store 200 may also include relationship information inferred from the genetic data stored in the genetic data store 205 and information received from the individuals. For example, the relationship information may indicate which individuals are genetically related, how they are related, how many generations back they share common ancestors, lengths and locations of IBD segments shared, which genetic communities an individual is a part of, variants carried by the individual, and the like.

The computing server 130 maintains genetic datasets of individuals in the genetic data store 205. A genetic dataset of an individual may be a digital dataset of nucleotide data (e.g., SNP data) and corresponding metadata. A genetic dataset may contain data of the whole or portions of an individual's genome. The genetic data store 205 may store a pointer to a location associated with the genealogical data store 200 associated with the individual. A genetic dataset may take different forms. In one embodiment, a genetic dataset may take the form of a base pair sequence of the sequencing result of an individual. A base pair sequence dataset may include the whole genome of the individual (e.g., obtained from a whole-genome sequencing) or some parts of the genome (e.g., genetic loci of interest).

In another embodiment, a genetic dataset may take the form of sequences of genetic markers. Examples of genetic markers may include target SNP loci (e.g., allele sites) filtered from the sequencing results. A SNP locus that is single base pair long may also be referred to a SNP site. A SNP locus may be associated with a unique identifier. The genetic dataset may be in a form of a diploid data that includes a sequencing of genotypes, such as genotypes at the target SNP loci, or the whole base pair sequence that includes genotypes at known SNP loci and other base pair sites that are not commonly associated with known SNPs. The diploid dataset may be referred to as a genotype dataset or a genotype sequence. Genotype may have a different meaning in various contexts. In one context, an individual's genotype may refer to a collection of diploid alleles of an individual. In other contexts, a genotype may be a pair of alleles present on two chromosomes for an individual at a given genetic marker such as a SNP site.

A genotype at a SNP site may include a pair of alleles. The pair of alleles may be homozygous (e.g., A-A or G-G) or heterozygous (e.g., A-T, C-T). Instead of storing the actual nucleotides, the genetic data store 205 may store genetic data that are converted to bits. For a given SNP site, oftentimes only two nucleotide alleles (instead of all 4) are observed. As such, a 2-bit number may represent a SNP site. For example, 00 may represent homozygous first alleles, 11 may represent homozygous second alleles, and 01 or 10 may represent heterozygous alleles. A separate library may store what nucleotide corresponds to the first allele and what nucleotide corresponds to the second allele at a given SNP site.

A diploid dataset may also be phased into two sets of haploid data, one corresponding to a first parent side and another corresponding to a second parent side. The phased datasets may be referred to as haplotype datasets or haplotype sequences. Similar to genotype, haplotype may have a different meaning in various contexts. In one context, a haplotype may also refer to a collection of alleles that corresponds to a genetic segment. In other contexts, a haplotype may refer to a specific allele at a SNP site. For example, a sequence of haplotypes may refer to a sequence of alleles of an individual that are inherited from a parent.

The individual profile store 210 stores profiles and related metadata associated with various individuals appeared in the computing server 130. A computing server 130 may use unique individual identifiers to identify various users and other non-users that might appear in other data sources such as ancestors or historical persons who appear in any family tree or genealogical database. A unique individual identifier may a hash of certain identification information of an individual, such as a user's account name, user's name, date of birth, location of birth, or any suitable combination of the information. The profile data related to an individual may be stored as metadata associated with an individual's profile. For example, the unique individual identifier and the metadata may be stored as a key-value pair using the unique individual identifier as a key.

An individual's profile data may include various kinds of information related to the individual. The metadata about the individual may include one or more pointer associating genetic datasets such as genotype and phased haplotype data of the individual that are saved in the genetic data store 205. The metadata about the individual may also individual information related to family trees and pedigree datasets that include the individual. The profile data may further include declarative information about the user that was authorized by the user to be shared and may also include information inferred by the computing server 130. Other examples of information stored in a user profile may include biographic, demographic, and other types of descriptive information such as work experience, educational history, gender, hobbies, or preferences, location and the like. In one embodiment, the user profile data may also include one or more photos of the users and photos of relatives (e.g., ancestors) of the users that are uploaded by the users. A user may authorize the computing server 130 to analyze one or more photos to extract information, such as user's or relative's appearance traits (e.g., blue eyes, curved hair, etc.), from the photos. The appearance traits and other information extracted from the photos may also be saved in the profile store. User profile data may also be obtained from other suitable sources, including historical records (e.g., records related to an ancestor), medical records, military records, photographs, other records indicating one or more traits, and other suitable recorded data.

For example, the computing server 130 may present various survey questions to its users from time to time. The responses to the survey questions may be stored at individual profile store 210. The survey questions may be related to various aspects of the users and the users' families. Some survey questions may be related to users' phenotypes, while other questions may be related to environmental factors of the users.

Survey questions may concern health or disease-related phenotypes, such as questions related to the presence or absence of genetic diseases or disorders, inheritable diseases or disorders, or other common diseases or disorders that have family history as one of the risk factors, questions regarding any diagnosis of increased risk of any diseases or disorders, and questions concerning wellness-related issues such as family history of obesity, family history of causes of death, etc. The diseases identified by the survey questions may be related to single-gene diseases or disorders that are caused by a single-nucleotide variant, an insertion, or a deletion. The diseases identified by the survey questions may also be multifactorial inheritance disorders that may be caused by a combination of environmental factors and genes. Examples of multifactorial inheritance disorders may include heart disease, Alzheimer's diseases, diabetes, cancer, and obesity. The computing server 130 may obtain data of a user's disease-related phenotypes from survey questions of health history of the user and her family and also from health records uploaded by the user.

Survey questions also may be related to other types of phenotypes such as appearance traits of the users. A survey regarding appearance traits and characteristics may include questions related to eye color, iris pattern, freckles, chin types, finger length, dimple chin, earlobe types, hair color, hair curl, skin pigmentation, susceptibility to skin burn, bitter taste, male baldness, baldness pattern, presence of unibrow, presence of wisdom teeth, height, and weight. A survey regarding other traits also may include questions related to users' taste and smell such as the ability to taste bitterness, asparagus smell, cilantro aversion, etc. A survey regarding traits may further include questions related to users' body conditions such as lactose tolerance, caffeine consumption, malaria resistance, norovirus resistance, muscle performance, alcohol flush, etc. Other survey questions regarding a person's physiological or psychological traits may include vitamin traits and sensory traits such as ability to sense an asparagus metabolite. Traits may also be collected from historical records, electronic health records and electronic medical records.

The computing server 130 also may present various survey questions related to environmental factors of users. In this context, an environmental factor may be a factor that is not directly connected to the genetics of the users. The environmental factors may also be referred to as the traits of the users. Environmental factors may include users' preferences, habits, and lifestyle. For example, a survey regarding users' preferences may include questions related to things and activities that users like or dislike, such as types of music a user enjoys, dancing preference, party-going preference, certain sports that a user plays, video games preferences, etc. Other questions may be related to the users' diet preference such as like or dislike a certain type of food (e.g., ice cream, egg). A survey related to habits and lifestyle may include questions regarding smoking habits, alcohol consumption and frequency, daily exercise duration, sleeping habits (e.g., morning person versus night person), sleeping cycles and problems, hobbies, and travel preferences. Additional environmental factors may include diet amount (calories, macronutrients), physical fitness abilities (e.g. stretching, flexibility, heart rate recovery), family type (adopted family or not, has siblings or not, lived with extended family during childhood), property and item ownership (has home or rents, has smartphone or doesn't, has car or doesn't).

Surveys also may be related to other environmental factors such as geographical, social-economic, or cultural factors. Geographical questions may include questions related to the birth location, family migration history, town or city of users' current or past residence. Social-economic questions may be related to users' education level, income, occupations, self-identified demographic groups, etc. Questions related to culture may concern users' religions, native language, language spoken at home, customs, dietary practices, etc. Other questions related to users' cultural and behavioral questions are also possible. Questions may also ask users' beliefs or opinions such as political beliefs, religious beliefs, opinions on certain debates, events, and controversies, and opinions on any suitable things or concepts. The beliefs and opinions may also be regarded as the traits of the users.

For any survey questions asked, the computing server 130 may also ask an individual the same or similar questions regarding the traits of the ancestors, family members, other relatives or friends of the individual. For example, a user may be asked about the native language of the user and the native languages of the user's parents and grandparents. A user may also be asked about the health history of his or her family members.

In addition to storing the survey data in the individual profile store 210, the computing server 130 may store some responses that correspond to data related to genealogical and genetics respectively to genealogical data store 200 and genetic data store 205.

The user profile data, survey response data, the genetic data, and the genealogical data may subject to the privacy and authorization setting from the users. For example, when presented with a survey question, a user may select to answer or skip the question. The computing server 130 may present users from time to time information regarding users' selection of the extent of information and data shared. The computing server 130 also may maintain and enforce one or more privacy settings for users in connection with the access of the user profile data, genetic data, and other sensitive data. For example, the user may pre-authorize the access of the data and may change the setting as wish. The privacy settings also may allow a user to specify (e.g., by opting out, by not opting in) whether the computing server 130 may receive, collect, log, or store particular data associated with the user for any purpose. A user may restrict her data at various levels. For example, in one level, the data may not be accessed by the computing server 130 for purposes other than displaying the data in the user's own profile. On another level, the user may authorize anonymization of her data and participate in studies and researches conducted by the computing server 130 such as a large scale genetic study. In yet another level, the user may turn some portions of her genealogical data public to allow the user to be discovered by other users (e.g., potential relatives) and be connected in one or more family trees. Access or sharing of any information or data in the computing server 130 may also be subject to one or more similar privacy policies.

The sample pre-processing engine 215 receives and pre-processes data received from various sources to change the data into a format used by the computing server 130. For genealogical data, the sample pre-processing engine 215 may receive data from an individual via the user interface 115 of the client device 110. To collect the user data (e.g., genealogical and survey data), the computing server 130 may cause an interactive user interface on the client device 110 to display interface elements in which users can provide genealogical data and survey data. Additional data may be obtained from scans of public records. The data may be manually provided or automatically extracted via, for example, optical character recognition (OCR) performed on census records, town or government records, or any other item of printed or online material. Some records may be obtained by digitalizing written records such as older census records, birth certificates, death certificates, etc.

The sample pre-processing engine 215 may also receive raw data from genetic data extraction service server 125. The genetic data extraction service server 125 may perform laboratory analysis of biological samples of users and generate sequencing results in the form of digital data. The sample pre-processing engine 215 may receive the raw genetic datasets from the genetic data extraction service server 125. The human genome mutation rate is estimated to be $1.1*10^{-8}$ per site per generation. This leads to a variant approximately every 300 base pairs. Most of the mutations that are passed down to descendants are related to single-nucleotide polymorphism (SNP). SNP is a substitution of a single nucleotide that occurs at a specific position in the genome. The sample pre-processing engine 215 may convert the raw base pair sequence into a sequence of genotypes of target SNP sites. Alternatively, the pre-processing of this conversion may be performed by the genetic data extraction service server 125. The sample pre-processing engine 215 identifies autosomal SNPs in an individual's genetic dataset. In one embodiment, the SNPs may be autosomal SNPs. In one embodiment, 700,000 SNPs may be identified in an individual's data and may be stored in genetic data store 205. Alternatively, in one embodiment, a genetic dataset may include at least 10,000 SNP sites. In another embodiment, a genetic dataset may include at least 100,000 SNP sites. In yet another embodiment, a genetic dataset may include at least 300,000 SNP sites. In yet another embodiment, a genetic dataset may include at least 1,000,000 SNP sites. The sample pre-processing engine 215 may also convert the nucleotides into bits. The identified SNPs, in bits or in other suitable formats, may be provided to the phasing engine 220 which phases the individual's diploid genotypes to generate a pair of haplotypes for each user.

The phasing engine 220 phases diploid genetic dataset into a pair of haploid genetic datasets and may perform imputation of SNP values at certain sites whose alleles are missing. An individual's haplotype may refer to a collection of alleles (e.g., a sequence of alleles) that are inherited from a parent.

Phasing may include a process of determining the assignment of alleles (particularly heterozygous alleles) to chromosomes. Owing to sequencing conditions and other constraints, a sequencing result often includes data regarding a pair of alleles at a given SNP locus of a pair of chromosomes but may not be able to distinguish which allele belongs to which specific chromosome. The phasing engine 220 uses a genotype phasing algorithm to assign one allele to a first chromosome and another allele to another chromosome. The genotype phasing algorithm may be developed based on an assumption of linkage disequilibrium (LD), which states that haplotype in the form of a sequence of alleles tends to cluster together. The phasing engine 220 is configured to generate phased sequences that are also commonly observed in many other samples. Put differently, haplotype sequences of different individuals tend to cluster together. A haplotype-cluster model may be generated to determine the probability distribution of a haplotype that includes a sequence of alleles. The haplotype-cluster model may be trained based on labeled data that includes known phased haplotypes from a trio (parents and a child). A trio is used as a training sample because the correct phasing of the child is almost certain by comparing the child's genotypes to the parent's genetic datasets. The haplotype-cluster model may be generated iteratively along with the phasing process with a large number of unphased genotype datasets. The haplotype-cluster model may also be used to impute one or more missing data.

By way of example, the phasing engine 220 may use a directed acyclic graph model such as a hidden Markov model (HMM) to perform phasing of a target genotype dataset. The directed acyclic graph may include multiple levels, each level having multiple nodes representing different possibilities of haplotype clusters. An emission probability of a node, which may represent the probability of having a particular haplotype cluster given an observation of the genotypes may be determined based on the probability distribution of the haplotype-cluster model. A transition probability from one node to another may be initially assigned to a non-zero value and be adjusted as the directed acyclic graph model and the haplotype-cluster model are trained. Various paths are possible in traversing different levels of the directed acyclic graph model. The phasing engine 220 determines a statistically likely path, such as the most probable path or a probable path that is at least more likely than 95% of other possible paths, based on the transition probabilities and the emission probabilities. A suitable dynamic programming algorithm such as the Viterbi algorithm may be used to determine the path. The determined path may represent the phasing result. U.S. patent application Ser. No. 15/519,099, entitled "Haplotype Phasing Models," filed on Oct. 19, 2015, describes one possible embodiment of haplotype phasing.

The IBD estimation engine 225 estimates the amount of shared genetic segments between a pair of individuals based on phased genotype data (e.g., haplotype datasets) that are stored in the genetic data store 205. IBD segments may be segments identified in a pair of individuals that are putatively determined to be inherited from a common ancestor. The IBD estimation engine 225 retrieves a pair of haplotype datasets for each individual. The IBD estimation engine 225 may divide each haplotype dataset sequence into a plurality of windows. Each window may include a fixed number of SNP sites (e.g., about 100 SNP sites). The IBD estimation engine 225 identifies one or more seed windows in which the alleles at all SNP sites in at least one of the phased haplotypes between two individuals are identical. The IBD estimation engine 225 may expand the match from the seed windows to nearby windows until the matched windows reach the end of a chromosome or until a homozygous mismatch is found, which indicates the mismatch is not attributable to potential errors in phasing or in imputation. The IBD estimation engine 225 determines the total length of matched segments, which may also be referred to as IBD segments. The length may be measured in the genetic distance in the unit of centimorgans (cM). A unit of centimorgan may be a genetic length. For example, two genomic positions that are one cM apart may have a 1% chance during each meiosis of experiencing a recombination event between the two positions. The computing server 130 may save data regarding individual pairs who share a length of IBD segments exceeding a predetermined threshold (e.g., 6 cM), in a suitable data store such as in the genealogical data store 200. U.S. patent application Ser. No. 14/029,765, entitled "Identifying Ancestral Relationships Using a Continuous stream of Input," filed on Sep. 17, 2013, and U.S. patent application Ser. No. 15/519,104, entitled "Reducing Error in Predicted Genetic Relationships," filed on Oct. 14, 2015, describe example embodiments of IBD estimation.

Typically, individuals who are closely related share a relatively large number of IBD segments, and the IBD segments tend to have longer lengths (individually or in aggregate across one or more chromosomes). In contrast, individuals who are more distantly related share relatively fewer IBD segments. These segments tend to be shorter (individually or in aggregate across one or more chromosomes). For example, while close family members often share upwards of 71 cM of IBD (e.g., third cousins), more distantly related individuals may share less than 12 cM of IBD. The extent of relatedness in terms of IBD segments between two individuals may be referred to as IBD affinity. For example, the IBD affinity may be measured in terms of the length of IBD segments shared between two individuals.

Community assignment engine 230 assigns individuals to one or more genetic communities based on the genetic data of the individuals. A genetic community may correspond to an ethnic origin or a group of people descended from a common ancestor. The granularity of genetic community classification may vary depending on embodiments and methods used in assigning communities. For example, in one embodiment, the communities may be African, Asian, European, etc. In another embodiment, the European community may be divided into Irish, German, Swedes, etc. In yet another embodiment, the Irish may be further divided into Irish in Ireland, Irish immigrated to America in 1800, Irish immigrated to America in 1900, etc. The community classification may also depend on whether a population is admixed or unadmixed. For an admixed population, the classification may further be divided based on different ethnic origins in a geographical region.

Community assignment engine 230 may assign individuals to one or more genetic communities based on their genetic datasets using machine learning models trained by unsupervised learning or supervised learning. In an unsupervised approach, the community assignment engine 230 may generate data representing a partially connected undirected graph. In this approach, the community assignment engine 230 represents individuals as nodes. Some nodes are connected by edges whose weights are based on IBD affinity between two individuals represented by the nodes. For example, if the total length of two individuals' shared IBD segments does not exceed a predetermined threshold, the nodes are not connected. The edges connecting two nodes are associated with weights that are measured based on the IBD affinities. The undirected graph may be referred to as an IBD network. The community assignment engine 230 uses clustering techniques such as modularity measurement (e.g., the Louvain method) to classify nodes into different clusters in the IBD network. Each cluster may represent a community. The community assignment engine 230 may also determine sub-clusters, which represent sub-communities. The computing server 130 saves the data representing the IBD network and clusters in the IBD network data store 235. U.S. patent application Ser. No. 15/168,011, entitled "Discovering Population Structure from Patterns of Identity-By-Descent," filed on May 28, 2016, describes one possible embodiment of community detection and assignment.

The community assignment engine 230 may also assign communities using supervised techniques. For example, genetic datasets of known genetic communities (e.g., individuals with confirmed ethnic origins) may be used as training sets that have labels of the genetic communities. Supervised machine learning classifiers, such as logistic regressions, support vector machines, random forest classifiers, and neural networks may be trained using the training set with labels. A trained classifier may distinguish binary or multiple classes. For example, a binary classifier may be trained for each community of interest to determine whether a target individual's genetic dataset belongs or does not belong to the community of interest. A multi-class classifier such as a neural network may also be trained to determine whether the target individual's genetic dataset most likely belongs to one of several possible genetic communities.

Reference panel sample store 240 stores reference panel samples for different genetic communities. A reference panel sample is a genetic data of an individual whose genetic data is the most representative of a genetic community. The genetic data of individuals with the typical alleles of a genetic community may serve as reference panel samples. For example, some alleles of genes may be over-represented (e.g., being highly common) in a genetic community. Some genetic datasets include alleles that are commonly present among members of the community. Reference panel samples may be used to train various machine learning models in classifying whether a target genetic dataset belongs to a community, in determining the ethnic composition of an individual, and in determining the accuracy in any genetic data analysis, such as by computing a posterior probability of a classification result from a classifier.

A reference panel sample may be identified in different ways. In one embodiment, an unsupervised approach in community detection may apply the clustering algorithm recursively for each identified cluster until the sub-clusters contain a number of nodes that is smaller than a threshold (e.g., contains fewer than 1000 nodes). For example, the community assignment engine 230 may construct a full IBD network that includes a set of individuals represented by nodes and generate communities using clustering techniques. The community assignment engine 230 may randomly sample a subset of nodes to generate a sampled IBD network. The community assignment engine 230 may recursively apply clustering techniques to generate communities in the sampled IBD network. The sampling and clustering may be repeated for different randomly generated sampled IBD networks for various runs. Nodes that are consistently assigned to the same genetic community when sampled in various runs may be classified as a reference panel sample. The community assignment engine 230 may measure the consistency in terms of a predetermined threshold. For example, if a node is classified to the same community 95% (or another suitable threshold) of times whenever the node is sampled, the genetic dataset corresponding to the individual represented by the node may be regarded as a reference panel sample. Additionally, or alternatively, the community assignment engine 230 may select N most consistently assigned nodes as a reference panel for the community.

Other ways to generate reference panel samples are also possible. For example, the computing server 130 may collect a set of samples and gradually filter and refine the samples until high-quality reference panel samples are selected. For example, a candidate reference panel sample may be selected from an individual whose recent ancestors are born at a certain birthplace. The computing server 130 may also draw sequence data from the Human Genome Diversity Project (HGDP). Various candidates may be manually screened based on their family trees, relatives' birth location, other quality control. Principal component analysis may be used to creates clusters of genetic data of the candidates. Each cluster may represent an ethnicity. The predictions of the ethnicity of those candidates may be compared to the ethnicity information provided by the candidates to perform further screening.

The ethnicity estimation engine 245 estimates the ethnicity composition of a genetic dataset of a target individual. The genetic datasets used by the ethnicity estimation engine 245 may be genotype datasets or haplotype datasets. For example, the ethnicity estimation engine 245 estimates the ancestral origins (e.g., ethnicity) based on the individual's genotypes or haplotypes at the SNP sites. To take a simple example of three ancestral populations corresponding to African, European and Native American, an admixed user may have nonzero estimated ethnicity proportions for all three ancestral populations, with an estimate such as [0.05, 0.65, 0.30], indicating that the user's genome is 5% attributable to African ancestry, 65% attributable to European ancestry and 30% attributable to Native American ancestry. The ethnicity estimation engine 245 generates the ethnic composition estimate and stores the estimated ethnicities in a data store of computing server 130 with a pointer in association with a particular user.

In one embodiment, the ethnicity estimation engine 245 divides a target genetic dataset into a plurality of windows (e.g., about 1000 windows). Each window includes a small number of SNPs (e.g., 300 SNPs). The ethnicity estimation engine 245 may use a directed acyclic graph model to determine the ethnic composition of the target genetic dataset. The directed acyclic graph may represent a trellis of an inter-window hidden Markov model (HMM). The graph includes a sequence of a plurality of node group. Each node group, representing a window, includes a plurality of nodes. The nodes representing different possibilities of labels of genetic communities (e.g., ethnicities) for the window. A node may be labeled with one or more ethnic labels. For example, a level includes a first node with a first label representing the likelihood that the window of SNP sites belongs to a first ethnicity and a second node with a second label representing the likelihood that the window of SNPs belongs to a second ethnicity. Each level includes multiple nodes so that there are many possible paths to traverses the directed acyclic graph.

The nodes and edges in the directed acyclic graph may be associated with different emission probabilities and transition probabilities. An emission probability associated with a node represents the likelihood that the window belongs to the ethnicity labeling the node given the observation of SNPs in the window. The ethnicity estimation engine 245 determines the emission probabilities by comparing SNPs in the window corresponding to the target genetic dataset to corresponding SNPs in the windows in various reference panel samples of different genetic communities stored in the reference panel sample store 240. The transition probability between two nodes represents the likelihood of transition from one node to another across two levels. The ethnicity estimation engine 245 determines a statistically likely path, such as the most probable path or a probable path that is at least more likely than 95% of other possible paths, based on the transition probabilities and the emission probabilities. A suitable dynamic programming algorithm such as the Viterbi algorithm or the forward-backward algorithm may be used to determine the path. After the path is determined, the ethnicity estimation engine 245 determines the ethnic composition of the target genetic dataset by determining the label compositions of the nodes that are included in the determined path. U.S. patent application Ser. No. 15/209,458, entitled "Local Genetic Ethnicity Determination System," filed on Jul. 13, 2016, describes an example embodiment of ethnicity estimation.

The front-end interface 250 may display various results determined by the computing server 130. The results and data may include the IBD affinity between a user and another individual, the community assignment of the user, the ethnicity estimation of the user, phenotype prediction and evaluation, genealogical data search, family tree and pedigree, relative profile and other information. The front-end interface 250 may be a graphical user interface (GUI) that displays various information and graphical elements. The front-end interface 250 may take different forms. In one case, the front-end interface 250 may be a software application that can be displayed at an electronic device such as a computer or a smartphone. The software application may be developed by the entity controlling the computing server 130 and be downloaded and installed at the client device 110. In another case, the front-end interface 250 may take the form of a webpage interface of the computing server 130 that allows users to access their family tree and genetic analysis results through web browsers. In yet another case, the front-end interface 250 may provide an application program interface (API).

Example Relative Connection Visualization Process

Figure 3:
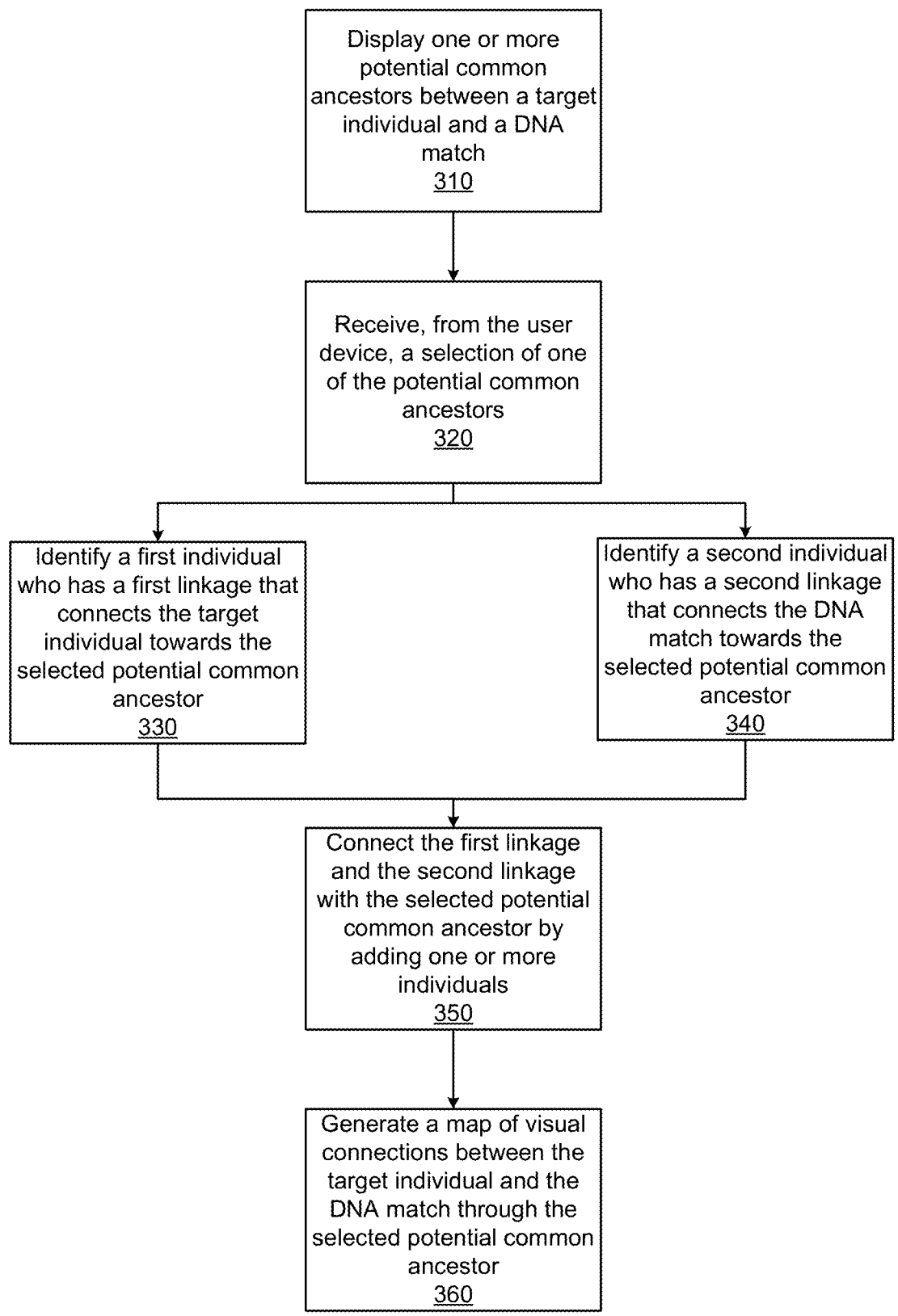
FIG. 3 is a flowchart depicting a process that generates visual connections of a target individual with a DNA match through a potential common ancestor, in accordance with an embodiment.

FIG. 3 illustrates a process that generates a map of visual connections between a target individual and a DNA match through a selected potential common ancestor. A target individual may be a user, a non-user, or any present or historical individual that has a record in the computing server 130. In one embodiment, the computing server 130 may identify one or more potential DNA matches for a target individual. A DNA match may be a DNA tester determined by computing server 130 to be likely related to the target individual. A DNA tester may be a user who has completed a DNA test that extracts DNA data of the user through, for example, genetic data extraction server 125, and has his or her genotype or haplotype data stored in the genetic data store 205. Using IBD estimation engine 235, the computing server 130 may determine the length of IBD segments shared by a user and another DNA tester. The computing server 130 may select one or more DNA testers as potential DNA matches of the individuals based on one or more suitable selection criteria. For example, the criteria may be the shared IBD segments being higher than a threshold, the two individuals being closely related in an IBD community as determined by community assignment engine 230, or other suitable conditions.

Figure 4:
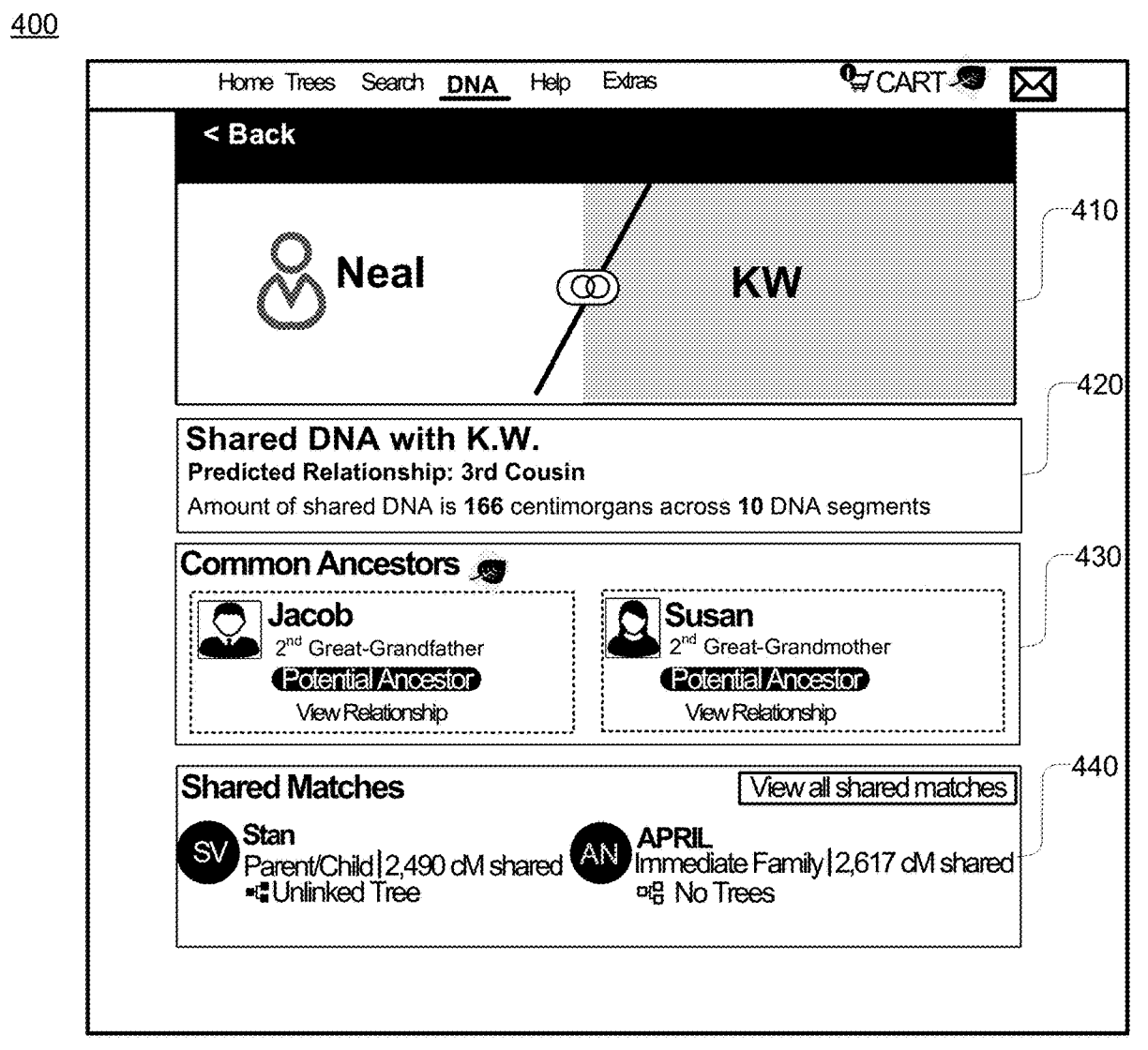

In one embodiment, in response to locating one or more DNA matches who grant permission for their profiles to be searchable, the computing server 130 may provide, through the front-end interface 250 generated at a client device 110, information of the DNA matches to the target individual, as shown in FIG. 4, whose details related to the graphical elements in the user interface 400 will be further discussed below. The computing server 130 may also transmit data for displaying 310 one or more potential common ancestors between the target individual and the DNA match in response to the user's request to view relationship between the target individual and the DNA match.

In one embodiment, a potential common ancestor may be identified through one or more family trees that are related to the target individual and/or the DNA match. The common ancestor may be a DNA tester, a non-DNA tester but user of the computing server, or a historical person in a genealogical record. In some cases, the computing server 130 may identify a potential common ancestor through a "big tree," which may be a large-scale network of individuals whose interrelationships are maintained and discovered by the computing server 130.

The computing server 130 may construct a large-scale network by concatenating a large number of family trees of different users. Various users, whether having their genetic data stored in computing server 130 or not, may have constructed one or more family data by using genealogy data store 200 to link individuals, such as DNA testers, other users of computing servers 130 who have not completed a DNA test, or historical individuals whose records are found in one or more genealogical data records. Based on users' permission to share the information, the computing server 130 may generate a large-scale network of individuals that include DNA testers, other users who have not completed DNA tests, and historical individuals. The large-scale network may include a very large number of people (such as many users of the computing server 130 and many other historical individuals who have been included in one or more family trees of users). The computing server 130 may collect a large number of family trees and link the trees together by identifying one or more common individuals in two or more trees.

In generating the large-scale network, the computing server 130 may encounter inconsistencies, contradictions, or other data irregularities that are present among various family trees. The computing server 130 may review the genealogical records to resolve those issues. Each individual, whether the individual is a user or a historical person, may be associated with a unique user identifier. In some embodiments, the computing server 130 may also train one or more machine learning models to determine whether different individuals with unique identifiers and being present in different genealogical records or family trees are in fact the same person. For example, the machine learning model may convert data of two individuals as feature vectors and input the feature vectors into the machine learning model to determine whether the individuals are the same person or to generate a confidence score that they are the same person. The computing server 130 may also train other machine learning models to determine the reliability of the data in a particular family tree or a particular genealogical data record to resolve potential conflicts among different family trees. When the computing server 130 determines a confidence that two nodes in two family trees represent the same person, the computing server 130 may concatenate the two trees by merging the nodes.

The computing server 130 may identify one or more potential common ancestors by using one or more family trees, such as using the large-scale network. For example, the computing server 130 may determine that the target individual and the DNA match are in fact connected in the large-scale network. The computing server 130 may identify one or more potential common ancestors who are in the path(s) connecting the target individual and the DNA match. Because one or more potential common ancestors may be identified through the large-scale network, those potential common ancestors may not be individuals who are listed in the target individual's genealogical profile, the DNA match's genealogical profile, or any of the two persons' family trees.

After the user selecting one of the DNA matches through a user interface, the computing server 130 may provide one or more suggestions of potential common ancestors to the target individual. The user has the option to select one of the potential common ancestors to further explore. The computing server 130 may receive 320 the user's selection and may start to retrieve connections that form a path between the target individual and the DNA match through the selected potential common ancestor. To complete a full connection, the computing server 130 may first identify 330 a connection who has a linkage that connects the target individual towards the selected potential common ancestor. The computing server 130 may identify 340 a connection who has a linkage that connects the DNA match towards the selected potential common ancestor. After one or more connections are retrieved and established, the above steps 330 and 340 may be repeated until the path between the target individual and the DNA match through the common ancestor is completed. Alternatively, or additionally, the computing server 130 may connect 350 the first linkage and the second linkage with the selected potential common ancestor by adding one or more individuals to complete the connection. The computing server 130 may generate 360 a map of visual connections between the target individual and the DNA match through the selected potential common ancestor.

Figure 5:
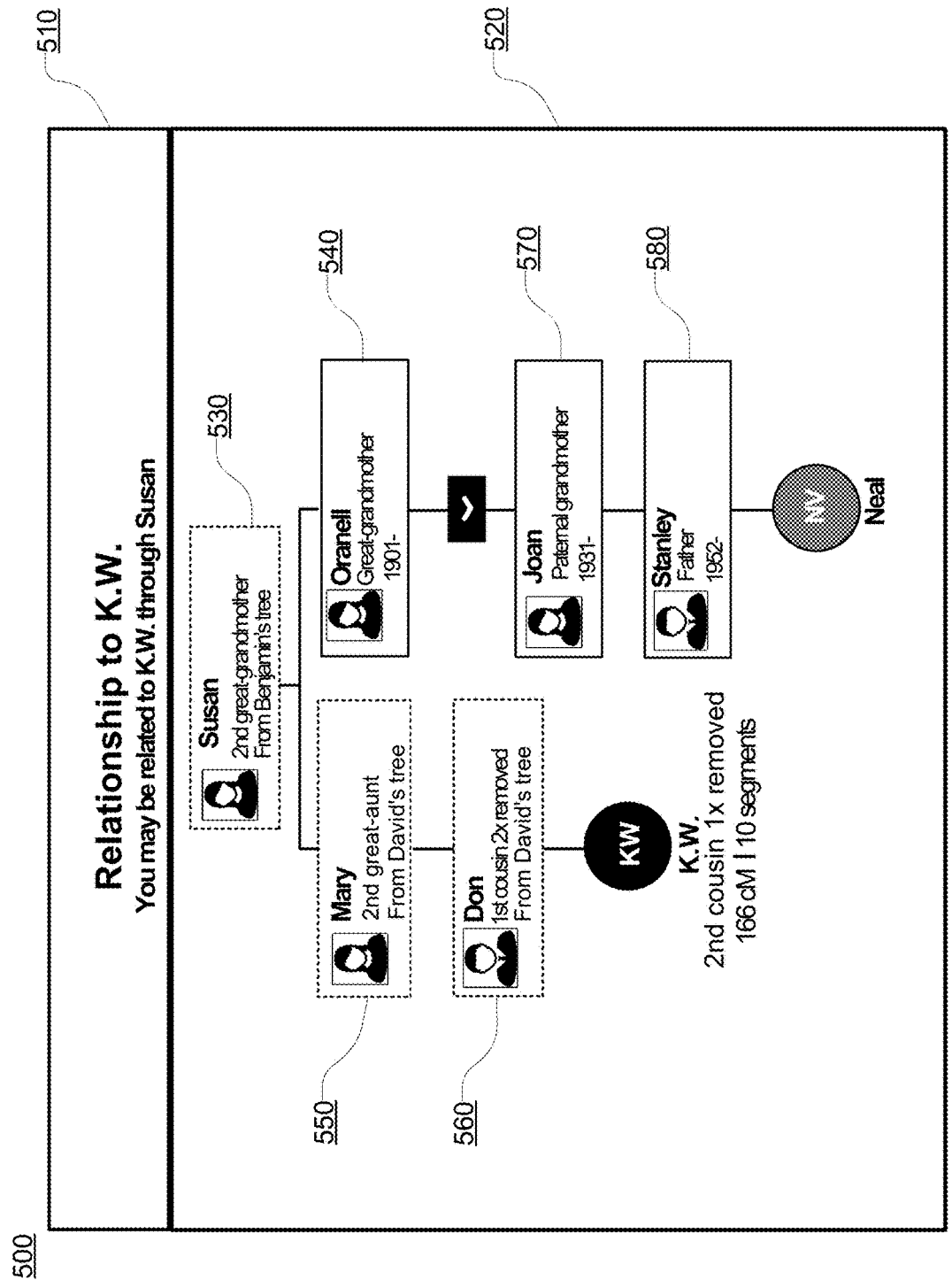
FIG. 5 is an example graphical user interface that displays visual connections between a target individual and a DNA match, in accordance with an embodiment.
Figure 6:
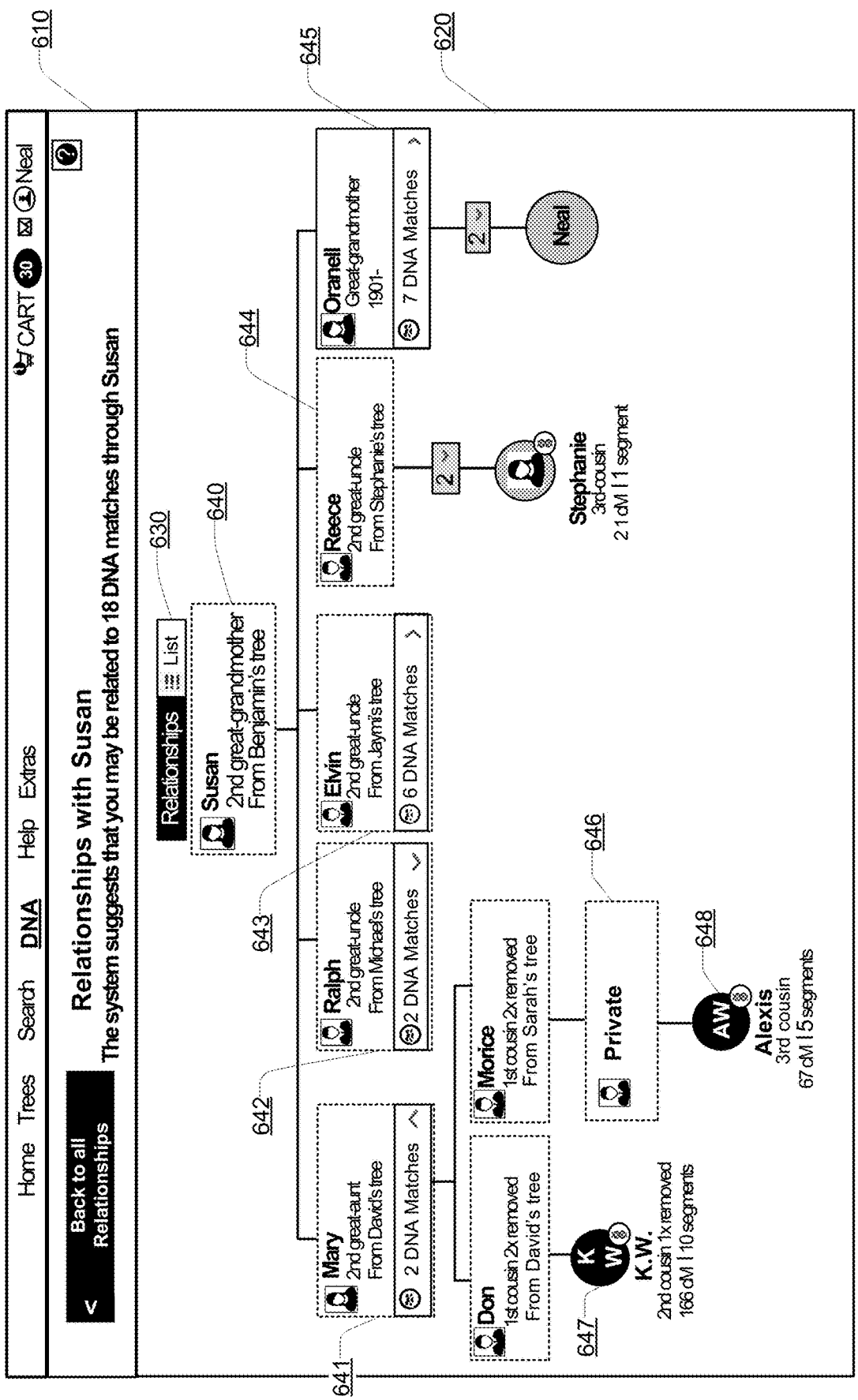
FIG. 6 is an example graphical user interface that displays an expanded view of visual connections of a common ancestor, in accordance with an embodiment.

The map of visual connections may take various forms. For example, FIG. 5, whose graphical elements will be discussed in further details below, shows an example of the map of visual connections that takes the form of a family tree that has only two branches. One branch displays the first linkage that connects the target individual towards the selected potential common ancestor. Another branch displays the second linkage that connects the DNA match towards the selected potential common ancestor. FIG. 6, whose graphical elements will also be discussed in further details below, shows another example of the map of visual connections of an expanded family tree, which may refer to an expanded map or a complete map. For example, the computing server 130 may receive a command from the user device to expand the map shown in FIG. 5. In turn, the computing server expands the map to a complete map, which includes the first and second branches showing respectively the first and second linkages and at least a third branch (if such branch is available) that includes additional descendants of the selected potential common ancestor. In various embodiments, other forms of map of visual connections, such as a starred connection, a meshed connection, a chained connection, a ring connection, and other suitable, regular or irregular, symmetric or not, cyclic or acyclic, directed or not, topologies are also possible. The form of map of visual connections may also not take the form of nodes and edges but, instead, in other forms such as grids, tabular forms, or other arrangements.

FIG. 4 is an example of a graphical user interface 400 for the user to view potential common ancestors and potential shared matches with respect to one of the target individual's DNA matches. For example, in this case, the computing server 130 may recommend a person KW to the user as a DNA match. The example user interface 400 shown in FIG. 4 may include an area 410 displaying profile pictures of the target individual and the DNA match. User interface 400 also may include an element 420 that displays predicted relationship between the target individual and the DNA match. Element 420 also displays the total length of matched DNA segments and the number of matched DNA segments determined by the IBD estimation engine 225. The length may be measured and displayed in the genetic distance in the unit of centimorgans (cM). The example user interface may also include element 430 that displays one or more potential common ancestors. The user may select one or more of the potential common ancestors and see how the target individual is connected with the DNA match through the selected common ancestor through a pedigree chart as shown in FIG. 5. User interface 400 may further include element 440 that displays common DNA matches who are related to both the target individual and the suggested DNA match along with their total length of matched DNA segments measured in the unit of centimorgans.

FIG. 5 is an example graphical user interface 500 for the user to view a path between the target individual and a DNA match, connecting through the common ancestor that the user selected through element 430. The path may be represented in different forms, such as in the form of a family tree as shown in user interface 500, a list, an acyclic graph that includes nodes and edges, and another suitable form. The user interface 500 may include a header 510 that indicates how the target individual Neal is connected with K. W. through a potential common ancestor Susan 530. In response to the user selecting the potential ancestor Susan 530 in element 430, the front-end interface 250 may display a family tree. The pedigree chart 520 connects Neal (the target individual) with KW (the DNA match) through Susan (the potential common ancestor).

Various types of relatives may be represented in the user interface 500 using different visual elements. In one embodiment, if a potential relative is not in the target individual's family tree, the user interface 500 may use a dotted lined box as the visual element to represent the relative. If a potential relative is in the target individual's family tree, the user interface 500 may use a solid lined box as the visual element to represent the potential common ancestor. For example, the potential ancestor Susan 530 is displayed with a dotted box around her name to indicate that she is not from the target individual Neal's tree. Instead, in this case, she is from Benjamin's tree, as indicated in element 530. Element 540 Oranell is displayed with a solid box around her name to indicate that she is from the target individual Neal's tree. Element 550 Mary is a potential DNA match with the target individual Neal. Because she is not in Neal's tree, her name is also presented within a dotted lined box. Element 550 also displays a potential relationship of the potential DNA match Mary and the target individual Neal. For example, in this case, Mary might be Neal's 2nd great-aunt. Similarly, element 560 shows that the potential DNA match Don might be the target individual Neal's 1st cousin twice removed. The family tree 520 may also include individuals such as Joan 570 and Stanley 580 who are confirmed to be in the target individual's family tree.

FIG. 6 is an example graphical user interface that illustrates an expanded family tree of the potential common ancestor Susan 640. Header 610 reads "Relationships for Susan" indicating that the map of visual connections displayed in user interface 620 are connected through the potential common ancestor Susan 640. Header 610 also indicates the total number of potential DNA matches through the potential common ancestor Susan 640. For example, in this case, 18 potential DNA matches are connected to the target individual through Susan 640.

The user interface 600 may provide various types of information related to confirmed relatives and potential relatives of the target individual. For example, in this case, the potential common ancestor Susan 640 is the root of the map of visual connections 620. Nodes 641 through 645 illustrate Susan 640's first generation of decedents. Each node 641 through 645 may also include information such as an individual's potential relationship with the target individual, the tree to which the individual belongs and the number of potential DNA matches through the individual. For instance, node 641 indicates that individual Mary may be the $2^{nd}$ great-aunt of the target individual Neal. Mary is from David's family tree. Two potential DNA matches 647 and 648 are discovered through the connection of Mary. Node 641 may also include a small upwards arrow, which indicates the branch of Mary's descendants is currently in its expanded view. A downward arrow or a rightward arrow such as the ones in nodes 642 and 643 may indicate that the branches are currently hidden. A user may click on a downward arrow or a rightward arrow to expand that branch. A user may also click on an upward arrow and hide the branch.

In one embodiment, a user who is authorized to manage an individual's account can protect the individual's personal information by setting the individual's tree to be private but searchable. By making this setting, information related to a private tree may still be accessible or searchable by the computing server 130. However, the computing server 130 does not display the identification information or only displays limited identification information of a private profile to other users. As a result, the individual's tree will be searchable by computing server 130 but the individual's information will not be available for other users to view. Node 646 is an example graphical element that may serve as a placeholder for a private person when viewed by other users. In this case individual 646 is displayed as private with no additional information of the individual presented. An individual may also set his/her tree to be private and not searchable. In that case, the computing server 130 will not use the individual's family tree when constructing connections.

User may choose a "Relationship" view or a "List" view through element 630 to toggle between two views. Element 620 shows an example of the "Relationship" view where FIG. 7 is a user interface example of the "List" view.

Figure 7:
FIG. 7 is an example graphical user interface that displays a list view of DNA matches, in accordance with an embodiment.

FIG. 7 is an example graphical user interface 700 that displays target individual's potential DNA matches in a list view. The computing server 130 may receive a command from the user to change a view of the map of visual connections. The computing server 130 may transmit for display a list of potentially related individuals. The list may replace the map of visual connections in the user interface. For example, a user may switch to this list view by clicking control element 721 "List." Example interface 700 includes a header 710 and a displaying area 720. The displaying area 720 shows a vertically ordered list of potential related individuals. For instance, in FIG. 7, displaying area 720 first includes a list of ordered blocks 722-726. Each block includes one of the potential common ancestor Susan 640's immediate offspring, ordered by age from the oldest to the youngest. For example, in this case, Mary is the oldest while Oranell is the youngest. Each element 722-726 may include one or more of potential DNA matches. For example, element 722 is the block for, Susan 640's oldest immediate offspring, Mary's family line. At the top right corner 722, the user interface 700 displays "2 matches" and an upward arrow. Mary's block 722 displays two potential DNA matches K. W. and Alexi. The upward arrow indicates that the list is currently expanded. A user may hide the list within the block 722 by clicking on the upward arrow. A user may also view the full connections with a DNA match by clicking the view relationship button. Blocks in displaying area 720 may also include each DNA match's potential relationship with the target individual and each DNA match's amount of shared DNA segments in centimorgan with the target individual.

Figure 8:
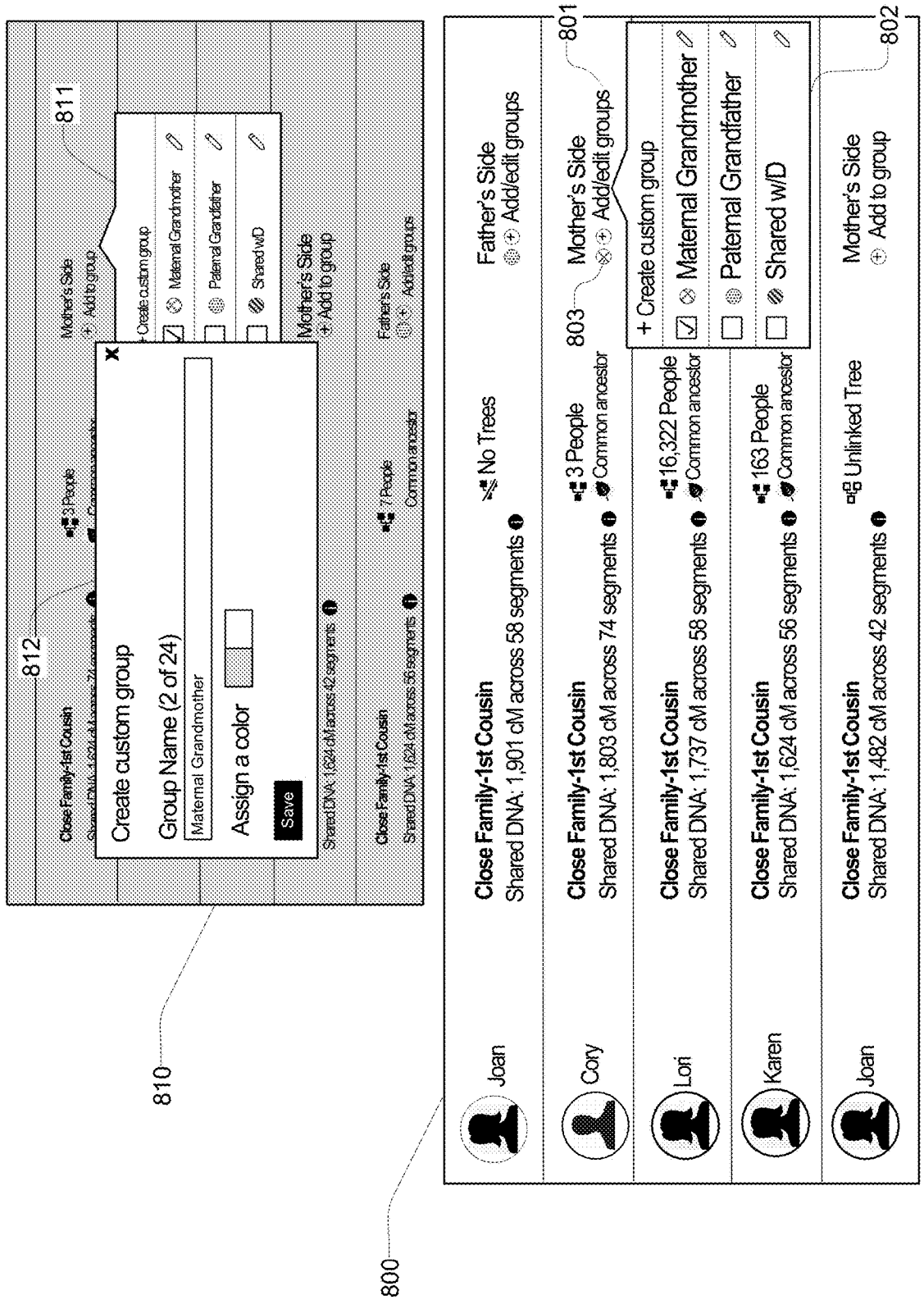
FIG. 8 is an example graphical user interface where a user can customize groups, in accordance with an embodiment.

FIG. 8 shows an example graphical user interface where a user may create custom groups and add DNA matches to existing custom groups. Each custom group has a unique graphical element as a representation of that custom group. In one embodiment, the user may add a DNA match to an existing custom group by clicking 801 "Add/edit groups." Responsive to the user clicking 801, a window 802 may pop out and overlay part of the displaying area 800. The user may click on one or more checkboxes in window 802 to assign the selected DNA match to the selected groups. When the selected DNA match is added to one or more selected groups, the unique graphical elements representing the selected groups will be displayed next to the person. For example, responsive to adding Cory in 800 to the custom group maternal grandmother through 802, element 803 shows up along with other information associated with Cory.

A user may also create a new custom group for a DNA match by clicking "create custom group" in the pop-up window 802. In response to user's request to create a new custom group, a window 812 may pop up which may overlay part of area 811 and area 810. Through window 812, the user may assign a name to the custom group and assign a color to the custom group, in one embodiment. In another embodiment, A user may also choose other distinguishable graphical elements to represent each custom group.

Figure 9B:
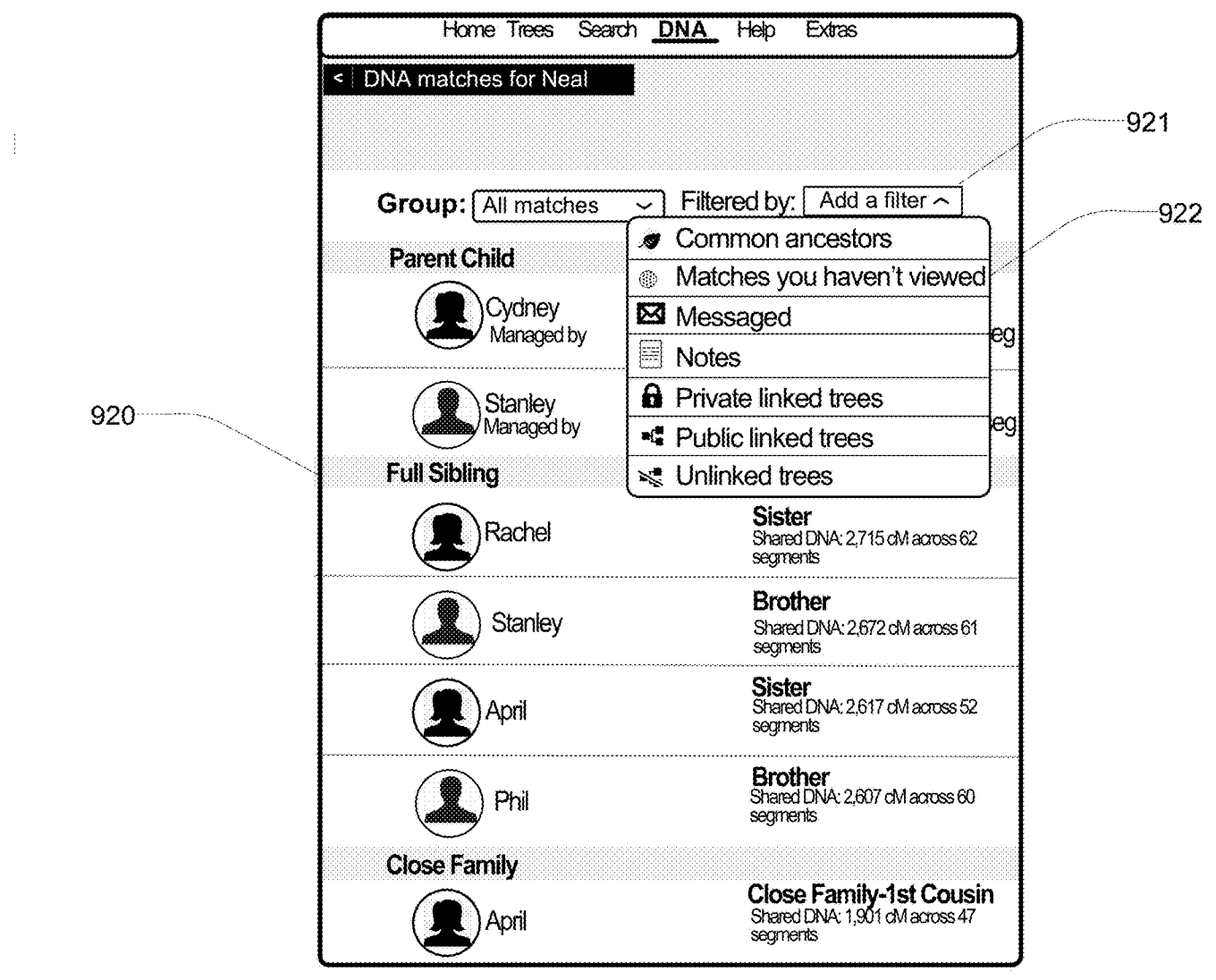

FIG. 9A through 9C are examples of user interface that illustrate various ways to view DNA matches. FIG. 9A is an example interface for a user to choose the DNA matches to view bases on groups. The user may click on element 911 in user interface 910 to open a window 912 which may overlay with interface 910. Within window 912, the user may select one or more groups. In response to user selecting the one or more groups, displaying area 910 will display DNA matches who belong to the selected groups.

FIG. 9B is an example interface for a user to choose the DNA matches to view based on filters. The user may click on element 921 in user interface 920 to open a window 922 which may overlay with interface 910. Within window 922, the user may select one or more criteria to enforce on the DNA matches. In response to the user selecting one or more criteria, displaying area 920 will display DNA matches who qualify the selected criteria. In one embodiment, a user may enforce multiple types of selecting criteria on the DNA matches. For example, a user may view all DNA matches from a certain group and further apply another filter to view the desired DNA matches. Potential filters may include, but not limited to, groups (e.g., user defined groups, system pre-set groups), viewed, notes, messages, private linked trees, public linked trees, unlinked trees, and common ancestors.

FIG. 9C shows an example interface 930 when a "common ancestor" filter 931 is applied to all DNA matches. The resulting individuals displayed are potential DNA matches who might share potential common ancestors with the target individual. The potential DNA matches are ordered vertically by their genetic similarity with the target individual, with the individual on the top being the most closely related with the target individual. Each DNA match is also displayed with the amount of shared DNA with the target individual.

The individuals may also be classified or tagged based on user's selections. The individuals in one or more map of visual connections shown in previous figures may be associated with metadata that are classified as groups and are displayed as color codes. The color codes may be displayed as tags that take the form of different colored circuits as shown in the rightmost column of FIG. 9C.

Example Genetic Evidence Evaluation Process for Relatedness

Figure 10:
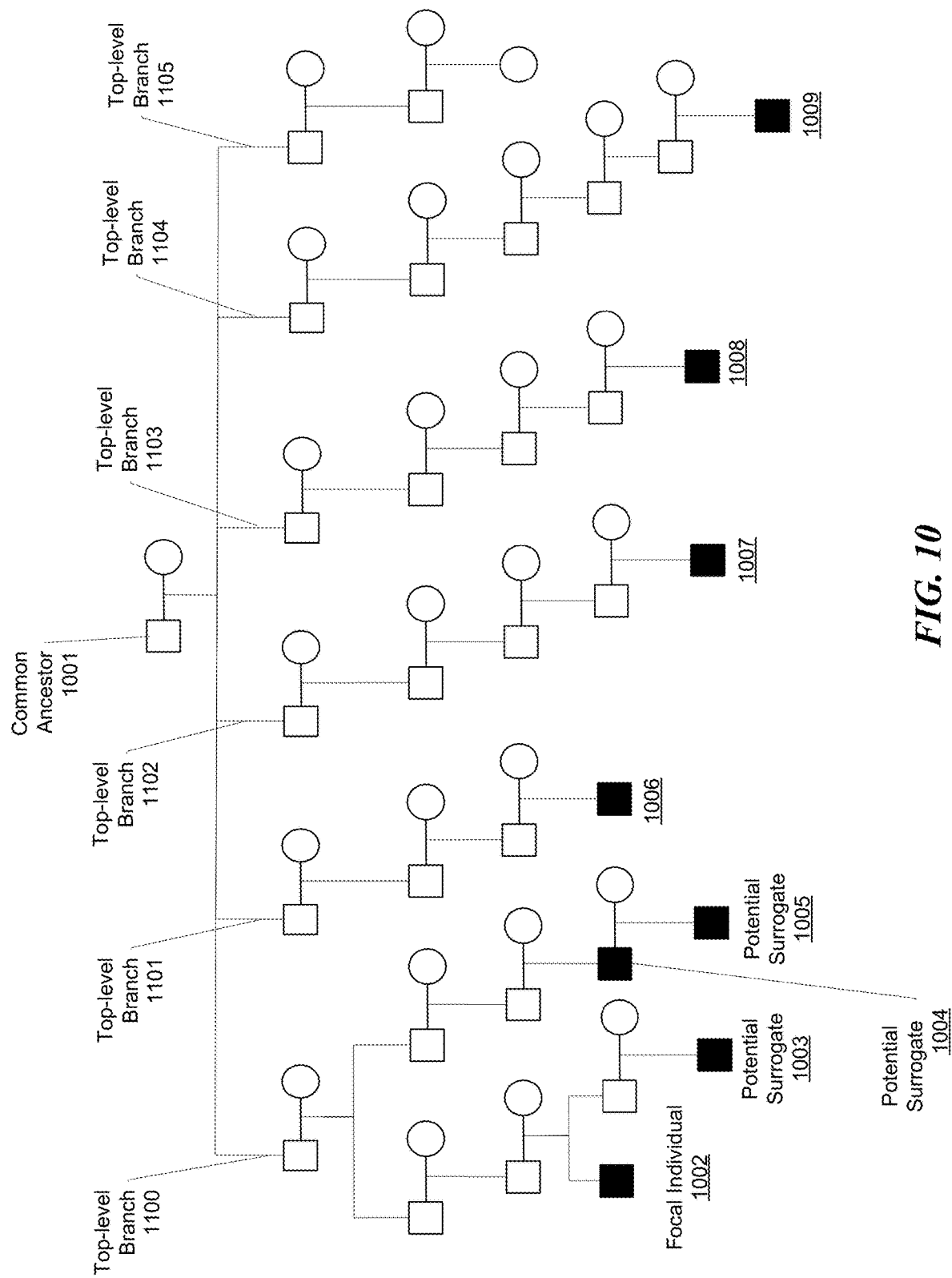
FIG. 10 illustrates a concatenated family tree chart including a focal individual and a common ancestor, in accordance with an embodiment.

FIG. 10 illustrates a concatenated family tree that may be combined from one or more family trees stored in the computing server 130. The expanded family tree 600 shown in FIG. 6 may be an example of the concatenated family tree. The family tree in FIG. 10 illustrates an example process for determining a confidence level of relatedness between a focal individual and a target potential relative, in accordance with an embodiment. The target potential relative may be a target potential ancestor.

For various reasons, a user of the genealogical and family tree system provided by the computing server 130 may desire to rely on genetic data to confirm the relatedness of potential relatives that are included in the user's family tree. For example, in one case, the user may, through a graphical user interface 115 (e.g., a web page, a mobile application, etc.), search the databases of the computing server 130 to identify one or more individuals who may be potential relatives of the user. The user may want to use genetic data to confirm the user's finding. In another case, the user may have already included an individual in the user's family tree, but would like to determine the precise relationship between the relative and the user. In yet another case, the potential relative may be suggested by the computing server 130 such as through the processes discussed in FIGS. 4 and 5.

In accordance with an embodiment, the user, through the user interface 115, may select an individual as a target potential relative to evaluate the relatedness between the user and the target potential relative based on the user's genetic data. The user may also be referred to as a focal individual. The computing server 130 receives the selection of the target potential relative. The computing server 130 may search through genealogical data store 205 to locate one or more family trees that include the target potential relative. For example, the target potential relative may be included in other users' public family trees. Those users may or may not be directly connected with the focal individual user. The computing server 130 retrieves one or more family trees that include the target potential relative. The family trees may include the family tree that is associated with the focal individual's profile and other family trees made available by other users. For the purpose of illustration, the retrieved one or more family trees may be concatenated to form a larger family tree as shown in FIG. 10. However, in various embodiments, the computing server 130 may not necessarily combine the retrieved family trees.

From the one or more family trees retrieved, the computing server 130 identifies descendants of the target potential relative who have genetic data available and stored in the genetic data store 210. Descendants in this context are individuals who are identified in one or more family trees as offspring of the target potential relative. Descendants may include potential descendants whose relationships with the target potential relative were input by a user when the user constructs his or her family tree but the relationships may not necessarily be verified. Descendants may also include verified descendants whose relationships with the target potential relative are confirmed. The computing server 130 may not have access to every descendant's genetic data in the retrieved family trees because not every person might have taken a genetic test or may have provided the computing server 130 access to the person's genetic data. The computing server 130 may identify, from the one or more retrieved family trees, descendants of the target potential relative who have genetic datasets available for the computing server 130. The identified descendants may include the focal individual. For example, in FIG. 10, the black squares may represent individuals who have genetic datasets available for the computing server 130.

The computing server 130 may identify one or more branches from the one or more family trees. Each of the identified branches may be a branch of descendants of the target potential relative. In various embodiments, the identified branches may include all the branches of the target potential relative or only a subset of the branches of the target potential relative. For example, in one embodiment, the computing server 130 may only identify branches that have at least one descendant who has the genetic dataset available for the computing server 130. In some cases, at least one of the identified branches is a cousin branch. A cousin branch in this context may be a branch whose descendants share the target potential relative as the most recent common ancestor (MRCA) with the focal individual. Put differently, any of the descendants in a cousin branch and the focal individual have the target potential relative as the MRCA. For example, in FIG. 10, five (1101-1105) out of six top-level branches are cousin branches. The leftmost top-level branch 1100 is not a cousin branch because the descendants in that branch share with the focal individual a common ancestor who is more recent than the target potential relative. In one case, the computing server 130 may identify all the five cousin branches. In another case, the computing server 130 may identify only some of the five cousin branches.

For each of the identified branches, the computing server 130 may identify one or more pairwise genetic relationships that are related to the branch. A pairwise genetic relationship may be a pair of descendants of the target potential relative. A pairwise genetic relationship related to a particular branch may be between a descendant of the branch and the focal individual or between a descendant of the branch and a surrogate of the focal individual. In one embodiment, the computing server 130 may identify only the pairwise genetic relationships that are sufficiently significant, such as those with the pairs who are sufficiently related by IBD. For example, the computing server 130 may retrieve, from the genetic data store 210, the genetic datasets for various descendants. The computing server 130 may compare any of the two descendants' genetic datasets and use phasing engine 220 and IBD estimation engine 225 to determine the length of the IBD segments that are shared by the two descendants. If the length of the IBD segments exceeds a threshold, the computing server 130 may determine that the two descendants are sufficiently related IBD and identify the pair as a pairwise genetic relationship. In another embodiment, the computing server 130 may identify any pairs of descendants that include one descendant from the branch, regardless of the length of the shared IBD segments between the pairs.

The computing server 130 may identify pairwise genetic relationships that are related to the focal individuals. For example, the related descendant may belong to a top-level branch in the concatenated family tree shown in FIG. 10 that is different from the branch to which the focal individual belongs. A descendant who shares the target potential relative with the focal individual as the MRCA may be referred to as a cousin. For example, a cousin in this context and the focal individual do not have a common ancestor who is a descendant of the target potential relative. The computing server 130 may determine a plurality of pairwise genetic relationships. One of the pairwise genetic relationships may be between the focal individual and a cousin.

In addition to or alternative to identifying pairwise genetic relationships involving the focal individual, the computing server 130 may use surrogates to identify other pairwise genetic relationships. Even though some of the descendants such as cousins may be related to the focal individual, other descendants, such as more distant relatives, may not share a sufficient amount of IBD segments with the focal individual. The computing server 130 may determine additional pairwise genetic relationships that include a surrogate and another descendant. The other descendant may or may not be sufficiently IBD related to the focal individual IBD. For example, descendant 1006 in FIG. 10 may be related to the focal individual 1002 IBD so that they form a strong pairwise genetic relationship. The descendant 1005 additionally may be related to a surrogate 1006 so that the computing system 130 also may capture this pairwise genetic relationship as well. In another example, the focal individual may share IBD segments with descendant 1008 for a length that is shorter than a threshold length to indicate that the focal individual is genetically related to the descendant 1008. However, the computing server 130 may identify descendant 1005 as a surrogate of the focal individual. The computing server 130 may capture the pairwise genetic relationship if the surrogate has shared IBD segments with the second descendant that are longer than the threshold length. In various embodiments, more than one surrogate may be identified and used as an intermediary for the focal individual.

A surrogate may be any descendant of the target potential relative in the one or more retrieved family trees that include the target potential relative. For a particular branch, the computing server 130 may identify any pairwise genetic relationships between a surrogate and another descendant who belongs to the particular branch. In various embodiments, the computing server 130 may include additional criteria in selecting a surrogate. In one embodiment, at least one surrogate of the focal individual is selected from descendants who have a length of shared IBD segments with the focal individual that exceeds a threshold length. In other words, the computing server 130 may choose relatives of the focal individuals as the surrogates. A surrogate may also be a close relative of the target potential relative. For example, a surrogate may have a length of shared IBD segments with the target potential relative that exceeds a threshold length. In another embodiment, a surrogate may be selected from one of the descendants who shares with the focal individual a common ancestor who is a descendant of the target potential relative. For example, the surrogate and the focal individual may belong to the same top-level branch. In yet another embodiment, the surrogate may be selected from one of the descendants who has information regarding a full family tree relationship between the surrogate and the target potential relative available in one of the family trees. A full family tree relationship may refer to information in the family trees that identifies every intermediate relative between the target potential relative and the surrogate. In other embodiments, the computing server 130 may identify surrogates based on additional, different, or any combinations of criteria.

The computing server 130 may score each identified pairwise genetic relationship to generate a plurality of relationship scores. A relationship score may be determined based on the genetic datasets of the pair of descendants in the pairwise genetic relationship. For example, a relationship score may be determined based on a length of the shared IBD segments between the pair of descendants in the pairwise genetic relationship. The length of the shared IBD segments, w, may be determined by phasing engine 220 and the IBD estimation engine 225. The computing server 130 may also determine the estimated degree of relatedness, m, between the pair of descendants in the pairwise genetic relationships as indicated by the family tree data. The score additionally may be based on the estimated degree of relatedness, m.

The estimated degree of relatedness may be determined based on an estimated number of meiosis separations between the pairs of descendants in a particular pairwise genetic relationship. The computing server 130 may count the estimated number of meiosis separations through a common ancestor between the pair of descendants. The computing server 130 first may identify the most recent common ancestor (MRCA) between the pair of descendants. For example, the estimated degree of relatedness between first cousins may be 4 because the MRCA in this example is one of the grandparents. The meiosis separations include (i) descendant A-parent A, (ii) parent A-common grandparent, (iii) common grandparent-parent B, and (iv) descendant B-parent B. In another example, the estimated degree of relatedness between an aunt-niece relationship may be 3 because the MRCA here is the parent of the aunt (grandparent of the niece). For more distant relationship or pairs that include more common ancestor couples, the estimated degree of relatedness may be calculated in any suitable ways such as based on the detailed framework set forth below in the Section entitled "Calculating m."

The relationship score for a pairwise genetic relationship may be determined based on both the length of the shared IBD segments, w, and the estimated degree of relatedness, m. In one embodiment, the relationship score may be or may correspond to a conditional probability of the estimated degree of relatedness, m, given the length of the shared IBD segments, w. The conditional probability may be denoted as Pr(m|w). In one embodiment, the values of the conditional probability may be determined based on the Bayes Law. For example, Pr(m|w)=Pr(w|m)*Pr(m)/Pr(w). In one embodiment, regarding Pr(w|m), the computing server 130 may retrieve known confirmed relatives from its genealogy data store 205 (e.g., known pairs of relative with a confirmed m) and determine the length of the shared IBD segments, w, using the phasing engine 220 and the IBD estimation engine 225. Based on a large number of known confirmed relatives, a distribution of Pr(w|m) may be determined and stored in a memory of the computing server 130. In one embodiment, regarding Pr(m), the computing server 130 may treat the degree of relatedness as uniformly distributed until m equals to a threshold number (e.g., m=12) that is too large to be considered the pair of relatives being related. In one embodiment, regarding Pr(w), the computing server 130 may sample the genetic data in the genetic data store 210 to build a distribution of the length of shared IBD segments among various users of the computing server 130. The distribution may be stored in a memory of the computing server 130. Based on the Bayes Law, the distribution of Pr(m|w) may be determined as a table and stored in a memory.

For each branch identified, the computing server 130 may combine one or more relationship scores to generate a combined relationship score that represents relatedness of the focal individual with the branch. The way how the combined relationship score is generated for each branch may depend on the number of pairwise genetic relationships that are related to the branch. In one case, the branch may have only one descendant who has genetic data available for the computing server 130. The computing server 130 may identify only a single pairwise genetic relationship between the focal individual and the descendant who has genetic data available. In such a case, the combined relationship score may be equal to the relationship score of the single pairwise genetic relationship. In another case, the branch may have a first pairwise genetic relationship between the focal individual and a first descendant and a second pairwise genetic relationship between the focal individual and a second descendant. In such a case, the computing may aggregate the relationship scores to generate the combined score. In one embodiment, the aggregation operation may include taking the maximum score out of the relationship scores as the combined score. In another embodiment, the aggregation operation may take a weighted average.

In yet another case, the computing server 130 may identify a plurality of pairwise genetic relationships for a particular branch. Some of the relationships are between the focal individual and one of the descendants in the branch, while other relationships are between one or more surrogates and one of the descendants in the branch. In such a case, the computing server 130 may combine the relationship scores with surrogate involved based on a chain of conditional probabilities and joint probabilities. The computing server 130 also may determine a weighted average of relationship scores. For example, a plurality of pairwise genetic relationships may include a first pairwise genetic relationship between one of the descendants in the branch and a first surrogate and a second pairwise genetic relationship between one of the descendants in the branch and a second surrogate. A first weight of the weighted average corresponding to the first pairwise genetic relationship may be determined based on a first relationship score between the focal individual of the first surrogate. A second weight of the weighted average corresponding to the second pairwise genetic relationship is determined based on a second relationship score between the focal individual of the second surrogate. The computing server 130 may also take maximum value to select among one or more relationship scores when appropriate. In one embodiment, the combined score may be determined based on one or more formulas below, in which F denotes the focal individual, C denotes a descendant in the branch, and S denotes a surrogate.

$$Score(F,C|S)=f(Score(F,C),Score(F,S),Score(S,C))$$

$$Score(F,C|S)=MAX(Score(F,C),Score(F,S)*Score(S,C))$$

$$Score(F,C|S)=w_0 Score(F,C)+w_1(Score(F,S)*Score(S,C))$$

$$Score(F,C|S)=g(Score(F,C|S_i)) 1<=i<=k$$

$$\text{Score}(F,C|S_i)=f(\text{Score}(F,C),\text{Score}(F,S_i),\text{Score}(S_i,C))$$

$$\text{Score}(F,C|S_i)=w_0\text{Score}(F,C)+\Sigma w_1(\text{Score}(F,S_i),\text{Score}(S_i,C))$$

In the equations above, g and $f$ can be any suitable functions. For example, the second equation may be a specific example of the generalized function $f$.

The computing server 130 may provide a result of the confidence level of relatedness between the focal individual and the target potential relative based on one or more of the combined relationship scores that represent relatedness of the focal individual with the one or more branches of descendants of the target potential relative. For example, the computing server 130 may provide a result that the focal individual is likely to be an offspring of the target potential relative or that the focal individual and the target potential relative are separated by, for example, six generations.

In some cases, how the confidence level is interpreted may be based on the degree of relatedness between the focal individual and the target potential relative. In one embodiment, the computing server 130 may determine, based on the one or more family trees retrieved, a degree of relatedness, m, between the focal individual and the target potential relative. The computing server 130, in response to the degree of relatedness between the focal individual and the target potential relative being lower than a threshold degree (e.g., m<6), the computing server 130 may determine the confidence level based on the maximum score among the one or more combined relationship scores. For more distant relationship between the focal individual and the target potential relative, the computing server 130 may determine the confidence level based on a number of the combined relationship scores (e.g., number>=3) that are larger than a threshold score. For example, the computing server 130 may indicate through the user interface 115 that the target potential relative is very likely to be a relative of the focal individual because there are at least three branches of descendants that support the relatedness.

In one embodiment, the computing server 130 may also determine the individual contributions of two or more pairwise genetic relationships to the result of the confidence level of relatedness. For example, the computing server 130 may identify several surrogates in the process. For each surrogate, the number of lines (e.g., the numbers of pairwise genetic relationships identified to be involving the surrogate) may also be considered to generate a confidence score associated with the surrogate. Some of the surrogates may significantly contribute to one or more high combined scores. The computing server 130 may determine the percentage contribution of the surrogates to the overall confidence level. The computing server 130 may display each of the individual contributions. For example, the computing server 130 may report X % direct match between the focal individual and descendants of the target relative, Y % match through surrogate 1, Z % match through surrogate 2. Through the user interface 115, the computing server 130 may also identify connected relatives of the focal individual who have large DNA segments that match a number of descendants of the target potential relatives'.

Calculating m

The evaluation of evidence depends on how m, the tree relationship, is calculated. For a simple case, which is a full relationship with only one pair of observed common ancestors, m is the number of hops between the two individuals (e.g., 1st cousins are m4).

More complicated relationships can be fit into the framework below. (1) For any half relationship between two individuals, use the m(x+1) distribution. (2) Inbreeding adds another path to the common ancestor couple. This acts the same as if there were a completely different ancestor. For example, m8wm6mg (m8 relationship with an m6 marriage in one of the lines) is the same as m8+m8. If the cousin marriage happens on a path that is longer than the closest path, then that is reflected accordingly (i.e. m8+m9). (3) 2m(x) is equal to m(x−1). That is, m8+m8=m7. (4) m(x)+m(x+1) is equal to a distribution halfway between the m(x) and m(x−1) distributions. In this case, the higher score between the distributions should be used. (5) m(x)+m(x+y) where y>1 is very close to the m(x) distribution. This distribution or the max between the m(x) and m(x−1) distributions could be used.

For example, consider the following relationship:
m7+m8+m8wm7mg+m9+m9wm6mg+m10+m10+m11

The above relationship can be simplified by first expanding the marriage inbreeding relationships:
m7+m8+m8+m9+m9+m9+m9+m10+m10+m11

The relationship can be further simplified by considering the combinations of relationships, highest relationships first:
m7+m8+m8+m9+m9+m9+m9+m9+m11
m7+m8+m8+m8+m9+m9+m9+m11
m7+m8+m8+m8+m8+m9+m11
m7+m7+m8+m8+m9+m11
m7+m7+m7+m9+m11
m6+m7+m9+m11

The relationship distribution is expected to be between the m6 and m7 distributions. The computing server 130 may run both m6 and m7 and take the maximum score.

Example Degree of Kinship Relatedness Process

Figure 11:
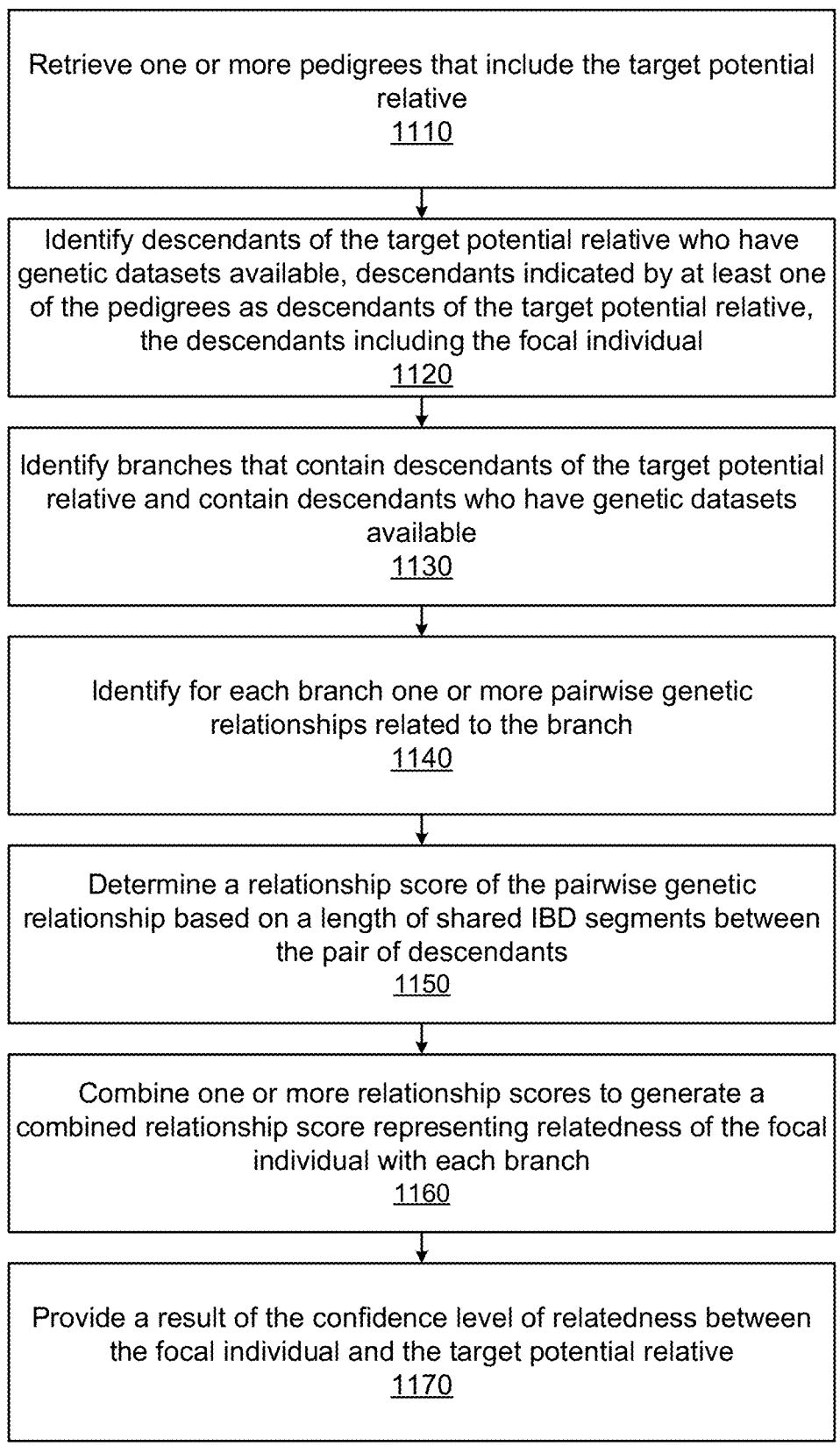
FIG. 11 is a flowchart depicting a process that provides results of a confidence interval of relatedness between a focal individual and a target potential relative, in accordance with an embodiment.

FIG. 11 is a flowchart depicting an example process 1100 for determining a confidence level of relatedness between a focal individual and a target potential relative. The process 1100 may include retrieving 1110 one or more pedigrees that include the target potential relative. The process may also include identifying 1120, from the one or more pedigrees, descendants of the target potential relative who have genetic datasets available, each descendant indicated by at least one of the pedigrees as a descendant of the target potential relative, the descendants including the focal individual. The process may further include identifying 1130 one or more branches from the one or more pedigrees, each of the identified branches being a branch of descendants of the target potential relative and including one or more descendants who have the genetic datasets available. The process may further include identifying 1140, for each branch, one or more pairwise genetic relationships related to the branch, wherein a pairwise genetic relationship is between two descendants of the target potential relative, and wherein a pairwise genetic relationship related to the branch is either (i) between one of the descendants in the branch and the focal individual or (ii) between one of the descendants in the cousin branch and a surrogate of the focal individual selected from one or more potential surrogates. The process may further include determining 1150, for each branch and each of the pairwise genetic relationships related to the branch, a relationship score of the pairwise genetic relationship based on a length of shared identity-by-descent (IBD) segments between the pair of descendants in the pairwise genetic relationship, the length of shared IBD segments determined from the genetic datasets of the pair. The process may further include 1160 combining, for each branch, one or more relationship scores to generate a combined relationship score representing relatedness of the focal individual with the branch. The process may further include providing 1170 a result of the confidence level of relatedness between the focal individual and the target potential relative based on one or more of the combined relationship scores that represent relatedness of the focal individual with the one or more branches of descendants of the target potential relative.

In one embodiment, at least one of the identified branches is a cousin branch. The cousin branch is a branch whose descendants share the target potential relative as a most recent common ancestor with the focal individual.

In one embodiment, one of the relationship scores corresponding to a particular pairwise genetic relationship may be determined based on a conditional probability of having an estimated degree of relatedness given the length of shared IBD segments between the pair of descendants in the particular pairwise genetic relationship.

In one embodiment, the estimated degree of relatedness may be determined based on an estimated number of meiosis separations between the pair of descendants in the particular pairwise genetic relationship.

In one embodiment, for at least one branch, generating the combined relationship score may include determining a weighted average of relationship scores of a plurality of pairwise genetic relationships, which includes a first pairwise genetic relationship between one of the descendants in the branch and a first surrogate and a second pairwise genetic relationship between one of the descendants in the branch and a second surrogate. A first weight of the weighted average corresponding to the first pairwise genetic relationship is determined based on a first relationship score between the focal individual of the first surrogate. A second weight of the weighted average corresponding to the second pairwise genetic relationship is determined based on a second relationship score between the focal individual of the second surrogate.

In one embodiment, at least one surrogate is selected from one of the descendants who has a length of shared IBD segments with the focal individual that exceeds a threshold length.

In one embodiment, at least one surrogate is selected from one of the descendants who has information regarding a full pedigree relationship between the surrogate and the target potential relative available in the one or more pedigrees.

In one embodiment, based on the genetic datasets, the focal individual has shared IBD segments with a particular descendant that are shorter than a threshold length to indicate that the focal individual is genetically related to the particular descendant. At least one surrogate has shared IBD segments with the particular descendant that are longer than the threshold length.

In one embodiment, at least one surrogate may be selected from one of the descendants who shares a common ancestor with the focal individual. The common ancestor may be a descendant of the target potential relative.

In one embodiment, the process 1100 may further include determining individual contributions of two or more pairwise genetic relationships to the result of the confidence level of relatedness. The process 1100 may further include displaying each of the individual contributions.

In one embodiment, providing the result of the confidence level of relatedness between the focal individual and the target potential relative based on the one or more of the combined relationship scores may include determining, based on the one or more pedigree, a degree of relatedness between the focal individual and the target potential relative.

Responsive to the degree of relatedness between the focal individual and the target potential relative being lower than a threshold degree, the computing server 130 may determine the confidence level based on a maximum score among the one or more of the combined relationship scores. Responsive to the degree of relatedness between the focal individual and the target potential relative being higher than a threshold degree, the computing server 130 may determine the confidence level based on a number of the combined relationship scores that are larger than a threshold score.

Computing Machine Architecture

Figure 12:
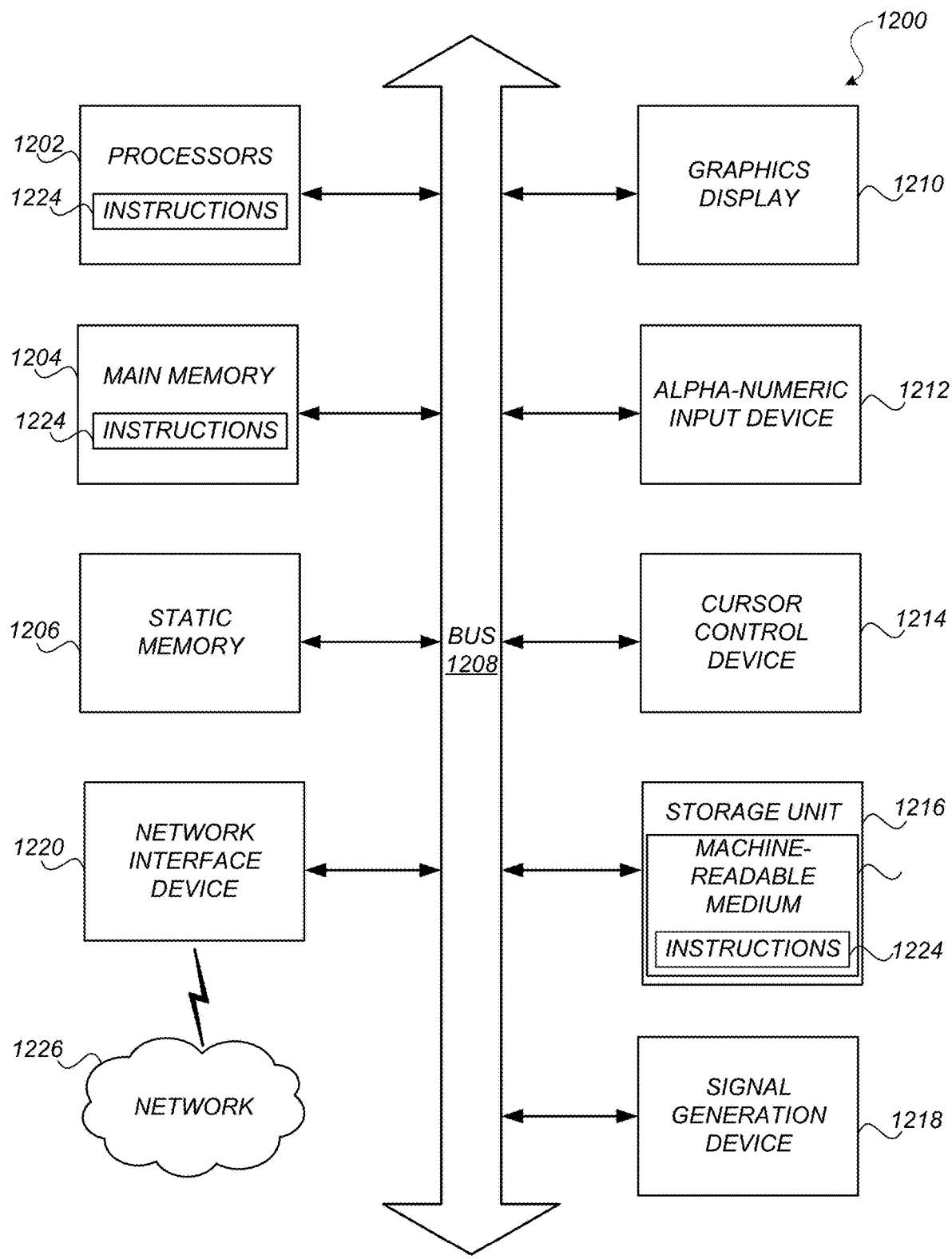
FIG. 12 is a block diagram illustrating example computer architecture, in accordance with an embodiment.

FIG. 12 is a block diagram illustrating components of an example computing machine that is capable of reading instructions from a computer-readable medium and execute them in a processor (or controller). A computer described herein may include a single computing machine shown in FIG. 12, a virtual machine, a distributed computing system that includes multiples nodes of computing machines shown in FIG. 12, or any other suitable arrangements of electronic devices.

By way of example, FIG. 12 shows a diagrammatic representation of a computing machine in the example form of a computer system 1200 within which instructions 1224 (e.g., software, program code, or machine code), which may be stored in a computer-readable medium for causing the machine to perform any one or more of the processes discussed herein may be executed. In some embodiments, the computing machine operates as a standalone device or may be connected (e.g., networked) to other machines. In a networked deployment, the machine may operate in the capacity of a server machine or a client machine in a server-client network environment, or as a peer machine in a peer-to-peer (or distributed) network environment.

The structure of a computing machine described in FIG. 12 may correspond to any software, hardware, or combined components shown in FIGS. 1 and 2, including but not limited to, the client device 110, the computing server 130, and various engines, interfaces, terminals, and machines shown in FIG. 2. While FIG. 12 shows various hardware and software elements, each of the components described in FIGS. 1 and 2 may include additional or fewer elements.

By way of example, a computing machine may be a personal computer (PC), a tablet PC, a set-top box (STB), a personal digital assistant (PDA), a cellular telephone, a smartphone, a web appliance, a network router, an internet of things (IoT) device, a switch or bridge, or any machine capable of executing instructions 1224 that specify actions to be taken by that machine. Further, while only a single machine is illustrated, the term "machine" and "computer" may also be taken to include any collection of machines that individually or jointly execute instructions 1224 to perform any one or more of the methodologies discussed herein.

The example computer system 1200 includes one or more processors 1202 such as a CPU (central processing unit), a GPU (graphics processing unit), a TPU (tensor processing unit), a DSP (digital signal processor), a system on a chip (SOC), a controller, a state equipment, an application-specific integrated circuit (ASIC), a field-programmable gate array (FPGA), or any combination of these. Parts of the computing system 1200 may also include a memory 1204 that store computer code including instructions 1224 that may cause the processors 1202 to perform certain actions when the instructions are executed, directly or indirectly by the processors 1202. Instructions can be any directions, commands, or orders that may be stored in different forms, such as equipment-readable instructions, programming instructions including source code, and other communication signals and orders. Instructions may be used in a general sense and are not limited to machine-readable codes. One or more steps in various processes described may be performed by passing through instructions to one or more multiply-accumulate (MAC) units of the processors.

One and more methods described herein improve the operation speed of the processors 1202 and reduces the space required for the memory 1204. For example, the database processing techniques and machine learning methods described herein reduce the complexity of the computation of the processors 1202 by applying one or more novel techniques that simplify the steps in training, reaching convergence, and generating results of the processors 1202. The algorithms described herein also reduces the size of the models and datasets to reduce the storage space requirement for memory 1204.

The performance of certain operations may be distributed among more than one processor, not only residing within a single machine, but being deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations. Even though in the specification or the claims may refer some processes to be performed by a processor, this should be construed to include a joint operation of multiple distributed processors.

The computer system 1200 may include a main memory 1204, and a static memory 1206, which are configured to communicate with each other via a bus 1208. The computer system 1200 may further include a graphical display unit 1210 (e.g., a plasma display panel (PDP), a liquid crystal display (LCD), a projector, or a cathode ray tube (CRT)). The graphical display unit 1210, controlled by the processors 1202, displays a graphical user interface (GUI) to display one or more results and data generated by the processes described herein. The computer system 1200 may also include alphanumeric input device 1212 (e.g., a keyboard), a cursor control device 1214 (e.g., a mouse, a trackball, a joystick, a motion sensor, or other pointing instrument), a storage unit 1216 (a hard drive, a solid-state drive, a hybrid drive, a memory disk, etc.), a signal generation device 1218 (e.g., a speaker), and a network interface device 1220, which are also configured to communicate via the bus 1208.

The storage unit 1216 includes a computer-readable medium 1222 that stores instructions 1224 embodying any one or more of the methodologies or functions described herein. The instructions 1224 may also reside, completely or at least partially, within the main memory 1204 or within the processor 1202 (e.g., within a processor's cache memory) during execution thereof by the computer system 1200, the main memory 1204 and the processor 1202 also constituting computer-readable media. The instructions 1224 may be transmitted or received over a network 1226 via the network interface device 1220.

While computer-readable medium 1222 is shown in an example embodiment to be a single medium, the term "computer-readable medium" should be considered to include a single medium or multiple medium (e.g., a centralized or distributed database, or associated caches and servers) able to store instructions (e.g., instructions 1224). The computer-readable medium may include any medium that is capable of storing instructions (e.g., instructions 1224) for execution by the processors (e.g., processors 1202) and that causes the processors to perform any one or more of the methodologies disclosed herein. The computer-readable medium may include, but not be limited to, data repositories in the form of solid-state memories, optical media, and magnetic media. The computer-readable medium does not include a transitory medium such as a propagating signal or a carrier wave.

Additional Considerations

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Any feature mentioned in one claim category, e.g. method, can be claimed in another claim category, e.g. computer program product, system, storage medium, as well. The dependencies or references back in the attached claims are chosen for formal reasons only. However, any subject matter resulting from a deliberate reference back to any previous claims (in particular multiple dependencies) can be claimed as well, so that any combination of claims and the features thereof is disclosed and can be claimed regardless of the dependencies chosen in the attached claims. The subject-matter may include not only the combinations of features as set out in the disclosed embodiments but also any other combination of features from different embodiments. Various features mentioned in the different embodiments can be combined with explicit mentioning of such combination or arrangement in an example embodiment or without any explicit mentioning. Furthermore, any of the embodiments and features described or depicted herein may be claimed in a separate claim and/or in any combination with any embodiment or feature described or depicted herein or with any of the features.

Some portions of this description describe the embodiments in terms of algorithms and symbolic representations of operations on information. These operations and algorithmic descriptions, while described functionally, computationally, or logically, are understood to be implemented by computer programs or equivalent electrical circuits, microcode, or the like. Furthermore, it has also proven convenient at times, to refer to these arrangements of operations as engines, without loss of generality. The described operations and their associated engines may be embodied in software, firmware, hardware, or any combinations thereof.

Any of the steps, operations, or processes described herein may be performed or implemented with one or more hardware or software engines, alone or in combination with other devices. In one embodiment, a software engine is implemented with a computer program product comprising a computer-readable medium containing computer program code, which can be executed by a computer processor for performing any or all of the steps, operations, or processes described. The term "steps" does not mandate or imply a particular order. For example, while this disclosure may describe a process that includes multiple steps sequentially with arrows present in a flowchart, the steps in the process do not need to be performed by the specific order claimed or described in the disclosure. Some steps may be performed before others even though the other steps are claimed or described first in this disclosure. Likewise, any use of (i), (ii), (iii), etc., or (a), (b), (c), etc. in the specification or in the claims, unless specified, is used to better enumerate items or steps and also does not mandate a particular order.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein. In addition, the term "each" used in the specification and claims does not imply that every or all elements in a group need to fit the description associated with the term "each." For example, "each member is associated with element A" does not imply that all members are associated with an element A. Instead, the term "each" only implies that a member (of some of the members), in a singular form, is associated with an element A. In claims, the use of a singular form of a noun may imply at least one element even though a plural form is not used.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights.

The following applications are incorporated by reference in their entirety for all purposes: (1) U.S. patent application Ser. No. 15/519,099, entitled "Haplotype Phasing Models," filed on Oct. 19, 2015, (2) U.S. patent application Ser. No. 15/168,011, entitled "Discovering Population Structure from Patterns of Identity-By-Descent," filed on May 28, 2016, (3) U.S. patent application Ser. No. 15/519,104 "Reducing Error in Predicted Genetic Relationships," filed on Oct. 14, 2015, (4) U.S. patent application Ser. No. 15/209,458, entitled "Local Genetic Ethnicity Determination System," filed on Jul. 13, 2016, and (5) U.S. patent application Ser. No. 14/029,765, entitled "Identifying Ancestral Relationships Using a Continuous stream of Input," filed on Sep. 17, 2013.

What is claimed is:

1. A computer-implemented method, comprising:
identifying a DNA match of a target individual;
identifying, in a network of individuals, a linkage between the DNA match and the target individual, wherein the network of individuals represents individuals as nodes in the network and is generated by concatenating a plurality of family trees of different individuals, wherein concatenating the plurality of family trees of different individuals to generate the network of individuals comprises:
retrieving a plurality of genealogical records corresponding to one or more individuals in the plurality of family trees,
identifying two or more genealogical records that are identified as potentially belonging to a particular individual,
generating a confidence score that the two or more genealogical records belong to the same particular individual, and
assigning a user identifier corresponding to the particular individual to the two or more genealogical records;
transmitting for display, at a graphical user interface, a predicted relationship between the DNA match and the target individual that is determined based at least on the linkage in the network identified between the DNA match and the target individual;
receiving, at the graphical user interface, a selection for the DNA match; and
generating a map of visual connections of the linkage to be displayed at the graphical user interface, the map comprising a first branch that connects the target individual with a potential common ancestor and a second branch that connects the DNA match with the potential common ancestor, wherein generating the map comprising concatenating a first family tree of the target individual that includes the first branch and a second family tree of the DNA match that includes the second branch.

2. The method of claim 1, wherein the network of individuals is a large-scale network that include the family trees of over 1,000 individuals.

3. The method of claim 1, wherein the individuals in the network of individuals comprises DNA testers, users who have not completed DNA tests, and historical individuals.

4. The method of claim 1, wherein concatenating the plurality of family trees of different individuals to generate the network of individuals further comprises:
detecting an inconsistency exists between two or more family trees;
reviewing genealogical records of the individuals in the two or more family trees that present the inconsistency; and
resolving the inconsistency to assign a unique user identifier to a common person present in the two or more family trees.

5. The method of claim 1, wherein concatenating the plurality of family trees of different individuals to generate the network of individuals further comprises:
determining that a first individual in a third family tree and a second individual in a fourth family tree are potentially the same individual;
converting data of the first individual to a first feature vector and data of the second individual to a second feature vector;
inputting the first feature vector and the second vector to a machine learning model; and
determining, by the machine learning model, whether the first individual and the second individual are in fact the same individual.

6. The method of claim 5, wherein concatenating the plurality of family trees of different individuals to generate the network of individuals further comprises:
assigning, responsive to determining that the first individual and the second individual are in fact the same individual, a unique identifier to the individual;
merging a first node representing the first individual and a second node representing the second individual as the same node; and
concatenating the third family tree containing the first individual and the fourth family tree containing the second individual.

7. The method of claim 1, further comprising:
receiving a command to expand the map; and
expanding the map to an expanded map, which comprises the first branch, the second branch, and a third branch including one or more additional descendants of the potential common ancestor.

8. The method of claim 1, wherein, in the map of visual connections, individuals who are potentially related to the target individual are displayed using a first graphical element and individuals who are confirmed to be related with the target individual are displayed using a second graphical element different from the first graphical element.

9. The method of claim 1, wherein one or more of the individuals in the map are displayed as private without revealing personal information.

10. The method of claim 1, further comprising:
adding, to a concatenated family tree concatenated from the first family tree and the second family tree, one or more individuals whose profiles are retrieved from other searchable genealogical profiles stored in an online system.

11. A system, comprising:
a computing server comprising memory and one or more processors, the memory storing instructions, the instructions, when executed by the one or more processors, cause the one or more processors to perform steps comprising:
identifying a DNA match of a target individual;
identifying, in a network of individuals, a linkage between the DNA match and the target individual, wherein the network of individuals represents individuals as nodes in the network and is generated by concatenating a plurality of family trees of different individuals, wherein concatenating the plurality of family trees of different individuals to generate the network of individuals comprises:
retrieving a plurality of genealogical records corresponding to one or more individuals in the plurality of family trees,
identifying two or more genealogical records that are identified as potentially belonging to a particular individual,
generating a confidence score that the two or more genealogical records belong to the same particular individual, and
assigning a user identifier corresponding to the particular individual to the two or more genealogical records; and
transmitting for display a predicted relationship between the DNA match and the target individual that is determined based at least on the linkage in the network identified between the DNA match and the target individual; and
a graphical user interface in communication with the computing server, the graphical user interface configured to:
receive a selection for the DNA match; and
display a map of visual connections of the linkage, the map comprising a first branch that connects the target individual with a potential common ancestor and a second branch that connects the DNA match with the potential common ancestor, wherein the map is generated by concatenating a first family tree of the target individual that includes the first branch and a second family tree of the DNA match that includes the second branch.

12. The system of claim 11, wherein the network of individuals is a large-scale network that include the family trees of over 1,000 individuals.

13. The system of claim 11, wherein the individuals in the network of individuals comprises DNA testers, users who have not completed DNA tests, and historical individuals.

14. The system of claim 11, wherein concatenating the plurality of family trees of different individuals to generate the network of individuals further comprises:
detecting an inconsistency exists between two or more family trees;
reviewing genealogical records of the individuals in the two or more family trees that present the inconsistency; and
resolving the inconsistency to assign a unique user identifier to a common person present in the two or more family trees.

15. The system of claim 11, wherein concatenating the plurality of family trees of different individuals to generate the network of individuals further comprises:
determining that a first individual in a third family tree and a second individual in a fourth family tree are potentially the same individual;
converting data of the first individual to a first feature vector and data of the second individual to a second feature vector;
inputting the first feature vector and the second vector to a machine learning model; and
determining, by the machine learning model, whether the first individual and the second individual are in fact the same individual.

16. The system of claim 15, wherein concatenating the plurality of family trees of different individuals to generate the network of individuals further comprises:
assigning, responsive to determining that the first individual and the second individual are in fact the same individual, a unique identifier to the individual;
merging a first node representing the first individual and a second node representing the second individual as the same node; and
concatenating the third family tree containing the first individual and the fourth family tree containing the second individual.

17. The system of claim 11, wherein the graphical user interface is further configured to:
receive a command to expand the map; and
expand the map to an expanded map, which comprises the first branch, the second branch, and a third branch including one or more additional descendants of the potential common ancestor.

18. The system of claim 11, wherein, in the map of visual connections, individuals who are potentially related to the target individual are displayed using a first graphical element and individuals who are confirmed to be related with the target individual are displayed using a second graphical element different from the first graphical element.

19. A non-transitory computer readable medium configured to store code comprising instructions, wherein the instructions, when executed by one or more processors, cause the one or more processors to perform steps comprising:
identifying a DNA match of a target individual;
identifying, in a network of individuals, a linkage between the DNA match and the target individual, wherein the network of individuals represents individuals as nodes in the network and is generated by concatenating a plurality of family trees of different individuals, wherein concatenating the plurality of family trees of different individuals to generate the network of individuals comprises:
retrieving a plurality of genealogical records corresponding to one or more individuals in the plurality of family trees,
identifying two or more genealogical records that are identified as potentially belonging to a particular individual,
generating a confidence score that the two or more genealogical records belong to the same particular individual, and
assigning a user identifier corresponding to the particular individual to the two or more genealogical records;
transmitting for display, at a graphical user interface, a predicted relationship between the DNA match and the target individual that is determined based at least on the linkage in the network identified between the DNA match and the target individual;
receiving, at the graphical user interface, a selection for the DNA match; and
generating a map of visual connections of the linkage to be displayed at the graphical user interface, the map comprising a first branch that connects the target individual with a potential common ancestor and a second branch that connects the DNA match with the potential common ancestor, wherein generating the map comprising concatenating a first family tree of the target individual that includes the first branch and a second family tree of the DNA match that includes the second branch.

20. The non-transitory computer readable medium of claim 19, wherein concatenating the plurality of family trees of different individuals to generate the network of individuals further comprises:
determining that a first individual in a third family tree and a second individual in a fourth family tree are potentially the same individual;
converting data of the first individual to a first feature vector and data of the second individual to a second feature vector;
inputting the first feature vector and the second vector to a machine learning model; and
determining, by the machine learning model, whether the first individual and the second individual are in fact the same individual.

\* \* \* \* \*